United States Patent [19]

Krause et al.

[11] Patent Number: 5,695,737
[45] Date of Patent: Dec. 9, 1997

[54] DIMERIC DTPA DERIVATIVES, THEIR METAL COMPLEXES AND PHARMACEUTICAL AGENTS CONTAINING THESE COMPLEXES

[75] Inventors: Werner Krause; Franz Karl Maier; Michael Bauer; Gabriele Schuhmann-Giampieri; Wolf Press; Johannes Platzek; Heribert Schmitt-Willich, all of Berlin, Germany

[73] Assignee: Schering Aktiengesellschaft, Berlin, Germany

[21] Appl. No.: 476,117

[22] Filed: Jun. 7, 1995

[30] Foreign Application Priority Data

Aug. 8, 1994 [DE] Germany .................. 44 28 874.3

[51] Int. Cl.⁶ .................. A61K 51/04; A61K 49/00; C07C 229/00; C07F 5/00
[52] U.S. Cl. .................. 424/1.65; 424/9.364; 534/10; 534/14; 534/16; 556/1; 556/50; 562/565
[58] Field of Search .................. 534/10, 14, 15, 534/16; 424/1.65, 9.364; 562/565; 556/1, 50

[56] References Cited

U.S. PATENT DOCUMENTS

| | | | |
|---|---|---|---|
| 4,647,447 | 3/1987 | Gries et al. | 424/9 |
| 4,826,673 | 5/1989 | Dean et al. | 424/9 |
| 4,915,933 | 4/1990 | Matwiyoff | 424/9 |
| 5,244,816 | 9/1993 | Subramanian | 436/545 |
| 5,274,076 | 12/1993 | Barbet et al. | 530/330 |
| 5,275,801 | 1/1994 | Niedballa et al. | 424/1.65 |
| 5,281,704 | 1/1994 | Love et al. | 540/465 |
| 5,284,647 | 2/1994 | Niedballa et al. | 424/81 |
| 5,330,743 | 7/1994 | Gibby et al. | 424/9 |
| 5,338,532 | 8/1994 | Tomalia et al. | 424/1.49 |
| 5,466,439 | 11/1995 | Gibby et al. | 424/9.365 |
| 5,482,700 | 1/1996 | Deutsch et al. | 424/9.364 |
| 5,517,993 | 5/1996 | Unger et al. | 128/653.4 |

FOREIGN PATENT DOCUMENTS

| | | |
|---|---|---|
| 305320 | 8/1988 | European Pat. Off. |
| 9205804 | 4/1992 | WIPO |

OTHER PUBLICATIONS

*Journal of General Chemistry*, vol. 60, No. 2, Part 2, Feb. 1990.

CA 113:58462 (1990)—Yashunskii et al., *Zh. Obshch. Khim.* 60 (2) 360–364, 1990.

CA 108:146368 (1987)—Lyubchanskii et al., SU 1127249, Oct. 15, 1987.

*Primary Examiner*—John Kight
*Assistant Examiner*—Lara C. Kelley
*Attorney, Agent, or Firm*—Millen, White, Zelano, & Branigan, P.C.

[57] ABSTRACT

The invention relates to new dimeric DTPA derivatives, their metal complexes, containing at least one ion of an element of atomic numbers 21–32, 37–39, 42–51 and 57–83, agents containing these complexes, their use in NMR diagnosis and/or diagnostic radiology, radiodiagnosis and radiotherapy, as well as process for their production.

23 Claims, No Drawings

DIMERIC DTPA DERIVATIVES, THEIR METAL COMPLEXES AND PHARMACEUTICAL AGENTS CONTAINING THESE COMPLEXES

The invention relates to the objects characterized in the claims, i.e., new dimeric DTPA derivatives and their metal complexes, pharmaceutical agents containing these complexes, their use in diagnosis and therapy as well as process for the production of complexes and agents.

Contrast media are indispensable additives in modern diagnosis; thus many diseases could not be diagnosed without the use of contrast media. Contrast media are used in all areas of diagnosis, such as, e.g., diagnostic radiology, radiodiagnosis or ultrasound diagnosis or magnetic resonance tomography.

The selection of the method preferred in each case depends, i.e., on the diagnostic problem, but is also determined by the choice of apparatus available in each case to the physician. Thus, because of the considerable technical expenditure and associated high cost, in particular nuclear spin topography has not yet found the wide use of other methods, such as, e.g., methods of diagnostic radiology.

The selection of the suitable contrast medium also varies on the basis of the respective problem. Thus, the suitability of the contrast medium for a specific object is determined last but not least by its (concentration) distribution behavior in the organism.

Although great progress has been achieved both on the equipment side and on the contrast medium side, solutions satisfactory for all problems are not yet available.

Thus, suitable contrast media do not exist for all indications for the various imaging processes. This holds true especially for computer tomography.

Paramagnetic metal complexes with aminopolycarboxylic acids were proposed in U.S. Pat. No. 4,647,447 (Gries et al.) as contrast media for NMR diagnosis, by which the gadolinium complex of diethylenetriaminepentaacetic acid (Gd-DTPA) has proven its value especially well as the diagnostic agent Magnevist® [H. P. Niendorf et al., Advances in MRI Contrast (1993); 2: 12–19]. It was also already proposed to use this mononuclear metal complex as x-ray contrast medium [C. Zwicker et al., Fortschr. Röntgenstr. 158, 3 (1993), 255–259], especially for patients who show a hypersensitivity to the iodine-containing contrast media used conventionally [Y. Kinno et al., A. J. R. (1993); 160: 1293–1294]. With respect to the higher mass attenuation coefficients, e.g., of the lanthanides relative to iodine, but the smaller absorption of a lanthanide atom in comparison with a triiodoaromatic compound, the synthesis of ligands, which are able to bond in a stable manner more than one metal atom per molecule, seems of great interest. The previous efforts in this outlook have not yet led to satisfactory results. Thus, the compounds described in WO 91/05762 [D. Love et al.] exhibit an inadequate heat- and long-term stability of the complex salt solutions. These complexes also leave something to be desired relative to their water solubility. This also holds true for the compounds proposed in WO 88/07521 [J. Deutsch et al.], whose compatibility is not yet satisfactory.

It has been found that the ligands that are novel in their structure according to the invention form metal complexes, which not only show high water solubility, but also surprisingly high compatibility and thus meet the requirements especially for an x-ray contrast medium suitable for bolus injections. But they are also very well suited as contrast media for NMR diagnosis and for radiodiagnosis and radiotherapy.

The new compounds according to the invention are described by general formula I—consisting of increments (A) and (B):

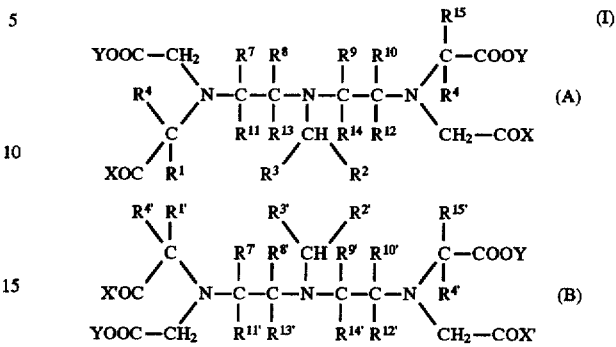

in which increments A and B are linked together by one of substituent pairs $R^1$ and $R^{1'}$, $R^2$ and $R^{2'}$, $R^{15}$ and $R^{15'}$, $R^1$ and $R^{2'}$, $R^{1'}$ and $R^2$, $R^{1'}$ and $R^{15}$, $R^1$ and $R^{15'}$, $R^2$ and $R^{15'}$, $R^{2'}$ and $R^{15}$, in which the substituent pair linked in each case stands for a heterocycle, a phenylene radical, a $C_0$–$C_{30}$ alkylene chain or a $C_7$–$C_{30}$ aralkylene chain, which optionally is substituted by 1-4 hydroxy, $C_1$–$C_6$ alkoxy, carboxy or mercapto groups and/or is interrupted by 1 to 6 oxygen, nitrogen, sulfur atoms, sulfinyl and/or sulfonyl groups, and which stand for substituents $R^1$, $R^{1'}$, $R^{15}$, $R^{15'}$ not required for linkage, independently of one another, for a hydrogen atom or a $C_1$–$C_6$ alkyl group optionally substituted by 1-4 hydroxy or mercapto groups, and which stand for substituents $R^2$ and $R^{2'}$ not required for linkage, independently of one another, for a hydrogen atom, a $C_1$–$C_6$ alkyl group, a group —$(CH_2)_n$OH or —$(CH_2)_n$SH with n=1 or 2, and substituents $R^3$ and $R^{3'}$, independently of one another, stand for a hydrogen atom, a group COOY, a $C_1$–$C_{30}$ alkyl chain or a $C_7$–$C_{30}$ aralkyl chain, which optionally is substituted by 1-4 hydroxy or $C_1$–$C_6$ alkoxy groups and/or is interrupted by 1-6 oxygen, nitrogen and/or sulfur atoms, or stand for a $CONR^5R^6$ group, in which $R^5$ and $R^6$, independently of one another, mean a $C_1$–$C_6$ alkyl group, which optionally is substituted by 1-4 hydroxy or $C_1$–$C_6$ alkoxy groups and/or is interrupted by 1-6 oxygen, nitrogen and/or sulfur atoms, or together with inclusion of the nitrogen atom form a 5- or 6-ring, which optionally contains an oxygen atom, another acylated nitrogen atom or a sulfonyl group and/or is substituted with 1-3 hydroxy groups, and substituents $R^4$ and $R^{4'}$ stand for a hydrogen atom and/or a $C_1$–$C_6$ alkyl group, and substituents $R^7$–$R^{14}$ and $R^{7'}$–$R^{14'}$ stand for a hydrogen atom, a phenyl group, a $C_1$–$C_{30}$ alkyl chain or a $C_7$–$C_{30}$ aralkyl chain, which optionally is substituted by 1-4 hydroxy, $C_1$–$C_6$ alkoxy or mercapto groups and/or is interrupted by 1-6 oxygen, nitrogen and/or sulfur atoms, or substituents $R^7$ and $R^8$, $R^{7'}$ and $R^{8'}$ or $R^9$ and $R^{10}$ and $R^{9'}$ and $R^{10'}$ together form a trimethylene or tetramethylene group, and Y respectively stands for a hydrogen atom and/or a metal ion equivalent of an element of atomic numbers 21–32, 37–39, 42–51 and 57–83, and X and X' stand for a group —OY, or —$CONR^5R^6$ with Y $R^5$ and $R^6$ in the mentioned meaning, as well as their salts with inorganic and/or organic bases or amino acids.

Compounds of general formula I—consisting of increments (A) and (B)—with Y meaning hydrogen are referred to as complexing agents and with at least two of substituents Y meaning a metal ion equivalent as metal complexes.

A $C_0$ alkylene chain is understood to mean a direct bond.

The elements of the mentioned atomic numbers also comprise (depending on the application sought) their radioactive isotopes.

If the agent according to the invention is intended for use in NMR diagnosis, the metal ion of the complex salt must be paramagnetic. These are especially the divalent and trivalent ions of the elements of atomic numbers 21–29, 42, 44 and 58–70. Suitable ions are, for example, the chromium(III), iron(II), cobalt(II), nickel(II), copper(II), praseodymium (III), neodymium(III), samarium(III) and ytterbium(III) ions. Because of their strong magnetic moment, gadolinium (III), terbium(III), dysprosium(III), holmium(III), erbium (III), iron(III) and manganese(II) ions are especially preferred.

For the use of the agents according to the invention in nuclear medicine, the metal ion must be radioactive. Suitable are, for example, radioisotopes of the elements copper, cobalt, gallium, germanium, yttrium, strontium, technetium, indium, ytterbium, gadolinium, samarium, iridium, rhenium and bismuth; preferred are technetium, gallium, indium and rhenium.

If the agent according to the invention is intended for use in diagnostic radiology, the metal ion is preferably derived from an element of a higher atomic number to achieve a sufficient absorption of x rays. It has been found that for this purpose, diagnostic agents which contain a physiologically compatible complex salt with metal ions of elements of atomic numbers 25 and 26 as well as 57–83 are suitable.

Preferred are manganese(II), iron(II), iron(III), praseodymium(III), neodymium(III), samarium(III), gadolinium(III), ytterbium(III) or bismuth(III) ions, especially dysprosium(III) ions.

The linkage of increments (A) and (B) takes place in each case with one of substituent pairs $R^1$ and $R^{1'}$, $R^2$ and $R^{2'}$, $R^{15}$ and $R^{15'}$, $R^1$ and $R^{2'}$, $R^{1'}$ and $R^2$, $R^{1'}$ and $R^{15}$, $R^1$ and $R^{15'}$, $R^2$ and $R^{15'}$, $R^{2'}$ and $R^{15}$.

The linkage preferably takes place with substituent pairs $R^1$ and $R^{1'}$, $R^2$ and $R^{2'}$ and $R^1$ and $R^{2'}$.

These bridge-type crosslinks consist of $C_0$–$C_{30}$ alkylene or $C_7$–$C_{30}$ aralkylene chains, which can be substituted by 1-4 hydroxy, $C_1$–$C_6$ alkoxy, carboxy or mercapto groups and/or can be interrupted by 1-6 oxygen, nitrogen or sulfur atoms or by sulfinyl or sulfonyl groups.

For substituent pair $R^2$ and $R^{2'}$, the direct bond ($C_0$ alkylene), the methylene, dimethylene and trimethylene, the benzylmethylene and benzyl ether groups are preferred.

Substituents $R^1$, $R^{1'}$, $R^{15}$, $R^{15'}$, not required for linkage, can, independently of one another, be hydrogen atoms and/or $C_1$–$C_6$ alkyl groups optionally substituted by 1-4 hydroxy or mercapto groups, substituents $R^2$ and $R^{2'}$ can, in addition, stand for a group —$(CH_2)_n$OH or —$(CH_2)_n$SH with n=1 or 2.

Substituents $R^3$ and $R^{3'}$, independently of one another, can stand for hydrogen atoms, for a COOY group, for a $C_1$–$C_{30}$ alkyl chain or a $C_7$–$C_{30}$ aralkyl chain, which optionally is substituted by 1-4 hydroxy or $C_1$–$C_6$ alkoxy groups and/or is interrupted by 1-6 oxygen, nitrogen and/or sulfur atoms or stand for a CONR$^5$R$^6$ group, in which R$^5$ and R$^6$ are the same or different and mean a $C_1$–$C_6$ alkyl group, which optionally is substituted by 1-4 hydroxy or $C_1$–$C_6$ alkoxy groups and/or is interrupted by 1-6 oxygen, nitrogen and/or sulfur atoms, or together with inclusion of the nitrogen atom form a 5- or 6-ring, which optionally contains an oxygen atom, another acylated nitrogen atom or a sulfonyl group and/or is substituted with 1-3 hydroxy groups. As examples, there can be mentioned 3,4-dihydroxypyrrolidine or (S,S-dioxo)-thiomorpholine.

Preferred substituents $R^3/R^{3'}$ are the carboxyl and carboxamide groups.

Substituents $R^4$ and $R^{4'}$ stand for hydrogen atoms and/or $C_1$–$C_6$ alkyl groups, and hydrogen atoms and methyl groups are preferred. Substituents $R^7$, $R^8$, $R^9$, $R^{10}$, $R^{11}$, $R^{12}$, $R^{13}$, $R^{14}$, $R^{4'}$, $R^{8'}$, $R^{9'}$, $R^{10'}$, $R^{11'}$, $R^{12'}$, $R^{13'}$ and $R^{14'}$ stand for a hydrogen atom, a phenyl group or a $C_1$–$C_{30}$ alkylene or aralkylene chain, which optionally is substituted by 1-4 hydroxy, $C_1$–$C_6$ alkoxy or mercapto groups and/or is interrupted by 1-6 oxygen, nitrogen or sulfur atoms.

Substituents $R^7$ and $R^8$, $R^{7'}$ and $R^{8'}$, $R^9$ and $R^{10}$ and $R^{9'}$ and $R^{10'}$ can, moreover, in each case together form a trimethylene or tetramethylene group.

Preferred substituents $R^7$–$R^{14}$ and $R^{7'}$–$R^{14'}$ are hydrogen atoms, methyl, ethyl and/or hydroxymethyl groups.

Substituents X and X' can both stand for a radical —OY and for a radical —CONR$^5$R$^6$ (with R$^5$/R$^6$ in the mentioned meaning).

Y stands for a hydrogen atom or a metal ion equivalent of an element of atomic numbers 21–32, 37–39, 42–51 and 57–83.

The production of the metal complexes according to the invention takes place in the way in which it was disclosed in Patent Application DE-OS 34 01 052, by the metal oxide or a metal salt (for example, the nitrate, acetate, carbonate, chloride or sulfate) of the element of atomic numbers 21–32, 37–39, 42–51, 57–83 being dissolved or suspended in water and/or a polar organic solvent, such as, e.g., DMF and/or methanol, ethanol or isopropanol and being reacted with the solution or suspension of the equivalent amount of the complexing acid of general formula I with Y meaning a hydrogen atom and then optionally present acid hydrogen atoms being substituted by cations of inorganic and/or organic bases or amino acids.

In this case, the neutralization takes place with the aid of inorganic bases (for example, hydroxides, carbonates or bicarbonates) of, for example, sodium, potassium, calcium or zinc and/or organic bases, such as, i.e., primary, secondary and tertiary amines, such as, for example, ethanolamine, morpholine, glucamine, N-methylglucamine and N,N-dimethylglucamine, as well as basic amino acids, such as, for example, lysine, arginine and ornithine.

For the production of neutral complex compounds, enough of the desired bases can be added, for example, to the acid complex salts in aqueous solution or suspension so that the neutral point is reached. The obtained solution can then be evaporated to dryness in a vacuum. Often, it is advantageous to precipitate the formed neutral salts by the addition of water-miscible solvents, such as, for example, lower alcohols (methanol, ethanol, isopropanol, and others), lower ketones (acetone and others), polar ethers (tetrahydrofuran, dioxane, 1,2-dimethoxyethane, and others) and thus to obtain easily isolated and readily purified crystallizates. It has proven especially advantageous to add the desired base as early as during the complexing of the reaction mixture and thus to save a process step.

If the acid complexes contain several free acid groups, it is often suitable to produce neutral mixed salts, which contain both inorganic and organic cations as counterions.

This can happen, for example, by the complexing acid being reacted in aqueous suspension or solution with the oxide or salt of the element supplying the central ion and half of the amount of an organic base required for neutralization, the formed complex salt being isolated, optionally purified and then mixed with the required amount of inorganic base for complete neutralization. The sequence of the addition of base can also be reversed.

In the case of using complex compounds containing radioisotopes, their production can be performed according to the methods described in "Radiotracers for Medical Applications," Volume 1, CRC Press, Boca Raton, Fla.

The production of the compounds according to the invention with Y meaning a hydrogen atom can take place in varied ways. The various processes are known in principle to one skilled in the art.

Thus, compounds of general formula I, for example; can be obtained in that the two primary amino groups of a diaminodicarboxylic acid of general formula II

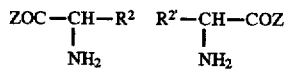  (II)

in which $R^2R^{2'}$ means a direct bond or a $C_1$-$C_{30}$ alkylene or a $C_7$-$C_{30}$ aralkylene chain, which optionally is substituted by hydroxy, $C_1$-$C_6$ alkoxy or mercapto groups and/or is interrupted by heteroatoms and Z stands for a group —$NR^5R^6$, in which $R^5$ and $R^6$ have the mentioned meaning, or for a functional group —OG, in which G means a hydrogen atom or a protective group, such as, for example, a tert-butyl or benzyl group, in which optionally present hydroxy groups are protected, for example, as acetals, are reacted with compounds of general formula III

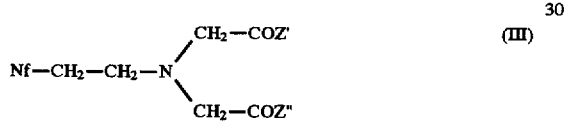  (III)

in which

Nf means a nucleofuge, such as, for example, chloride, bromide or iodide, and

Z' and Z", independently of one another, have the meaning indicated for Z and in that after cleavage of the protective groups, a polycarboxylic acid of general formula IV

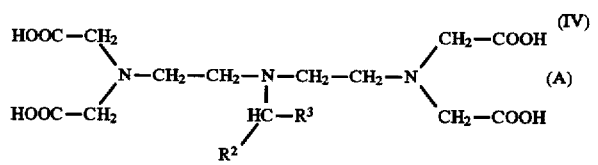  (IV)

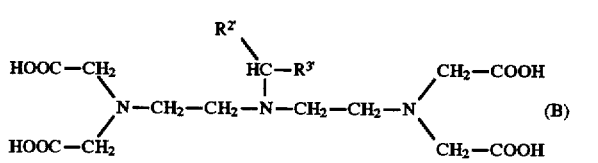

is obtained, with $R^2R^{2'}$ meaning a $C_0$-$C_{30}$ alkylene or a $C_7$-$C_{30}$ aralkylene chain, which optionally is substituted by 1-4 hydroxy, $C_1$-$C_6$ alkoxy, carboxy or mercapto groups and/or is interrupted by oxygen, nitrogen and/or sulfur atoms or by a sulfinyl or sulfonyl group and is converted with $R^3$ and $R^{3'}$ in the mentioned meaning and the compounds of formula IV then optionally to a salt of an inorganic and/or organic base or amino acid. Optionally, a part of the carboxy groups according to their activation and reaction can be converted to amide groups with an amine of general formula V $$HNR^5R^6 \qquad (V)$$

with $R^5$ and $R^6$ in the mentioned meaning.

If the synthesis is performed starting from a sulfur-containing diaminodicarboxylic acid of general formula II meaning, for example, cystathionine or lanthionine, the thio ether groups can optionally be converted in a way known in the art by suitable oxidizing agents, such as hydrogen peroxide or peracids, preferably before cleavage of optionally present protective groups to the corresponding sulfinyl or sulfonyl compounds.

Compounds of general formula IV are also attained by a dicarboxylic acid of general formula VI

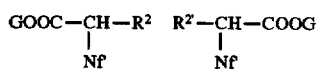  (VI)

in which $R^2R^{2'}$ and G have the above-mentioned meaning and Nf stands for a nucleofuge, such as, e.g., a chloride, bromide, iodide, O-mesylate, O-tosylate or O-triflate, being reacted in a way known in the art with the bis-(2-phthalimidoethyl)-amine to a tetraphthalimido compound of general formula VII

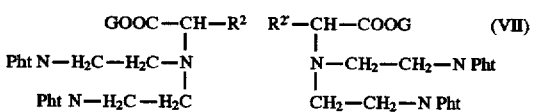  (VII)

in which $R^2R^{2'}$ has the mentioned meaning and NPht stands for a phthalimido group.

After cleavage of these protective groups, a dipiperazino derivative of general formula VIII

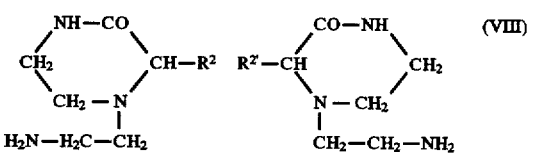  (VIII)

with $R^2R^{2'}$ in the above-mentioned meaning, from which a compound of general formula X

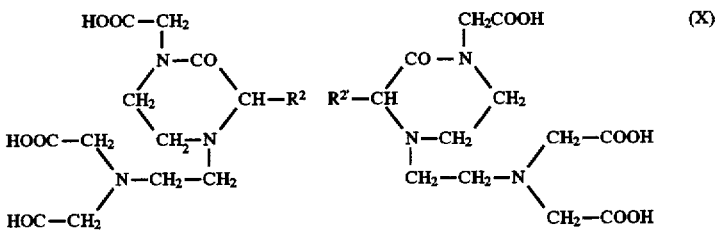 (X)

with R²R²' in the mentioned meaning is obtained with a reactant of general formula IX

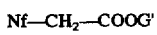 (IX)

with Nf meaning chloride, bromide or iodide and G' meaning G with the exception of hydrogen, is obtained after cleavage of the protective groups.

The obtained hexacarboxylic acid is then subjected in succession to a lactam cleavage and an N-alkylation with a reactant of general formula XI,

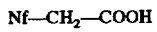 (XI)

in which Nf has the mentioned meaning, and a compound of general formula IV, with R²R²' in the mentioned meaning and R³ and R³' meaning a carboxyl group, is obtained.

Another type of synthesis control consists in the fact that starting from an amino acid carrying hydroxy or mercapto group(s) and optionally present as ester, such as, for example, L-tyrosine benzyl ester, and by alkylation with a compound of general formula III, a compound of general formula XII

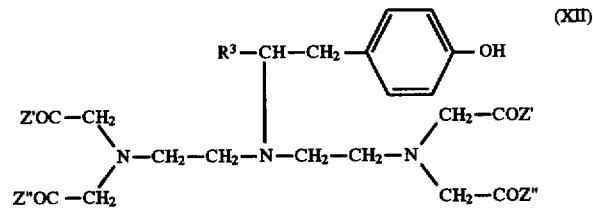 (XII)

with R³, Z' and Z" in the above-mentioned meaning, is produced and then linked like ether by O-alkylation with a bifunctional alkylating agent, such as, for example, 1-8-diiodooctane, in each case two molecules of general formula XII and below optionally present protective groups are cleaved.

In another type of synthesis control, a start is made from a diamine of general formula XIII from

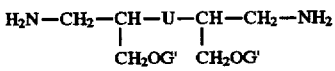 (XIII)

with G' in the above-mentioned meaning of a protective group for hydroxy functions, and U meaning a direct bond or a $C_1$-$C_{30}$ alkylene or a $C_7$-$C_{30}$ aralkylene chain, which optionally is substituted by 1-4 hydroxy, $C_1$-$C_6$ alkoxy or mercapto groups and/or is interrupted by 1-6 oxygen, nitrogen or sulfur atoms. The latter is alkylated with an electrophile of general formula III. Finally, optionally present protective groups are cleaved in the usual way.

In another variant of the synthesis control, a tetraoxazoline derivative is obtained starting from a compound of formula II, with R²R²' and Z in the above-mentioned meaning, by alkylation with a compound of general formula XIV

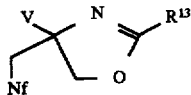 (XIV)

in which $R^{13}$ means a $C_1$-$C_6$ alkyl group, V means a group $R^{11}$, $R^{11'}$ $R^{12}$ or $R^{12'}$ and Nf has the mentioned meaning. Compounds of formula XIV can be obtained, for example, from a serinol derivative of general formula XV

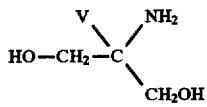 (XV)

in which V has the mentioned meaning.

From the tetraoxazoline derivative, a hexamine of general formula XVI

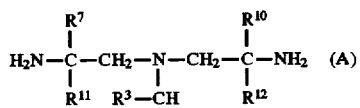 (XVI)

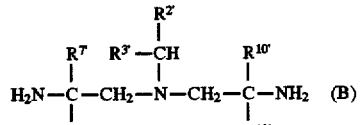

is obtained by hydrolysis, in which R²R²' means a direct bond or a $C_1$-$C_{30}$ alkylene chain or a $C_7$-$C_{30}$ aralkylene chain, which optionally is substituted by hydroxy, $C_1$-$C_6$ alkoxy or mercapto groups, and/or is interrupted by 1-6 oxygen, nitrogen or sulfur atoms, and in which $R^3$, $R^{3'}$, $R^7$, $R^{7'}$, $R^{10}$, $R^{10'}$, $R^{11}$, $R^{11'}$, $R^{12}$, $R^{12'}$ have the mentioned meaning. The hexamine of formula XVI is then alkylated with a haloacetic acid, which optionally is present in protected form, for example as tert-butyl ester. Present protective groups are then cleaved in a way known in the art.

In another type of synthesis control, a start is made from a diamine of general formula II and an N,N'-protected diamine of such type as can also be obtained, for example, by reaction of an α,α'-dihalogendicarboxylic acid with, e.g., benzylamine, is obtained by reaction of amino groups with an aromatic aldehyde, such as, for example, benzaldehyde and subsequent reduction, for example, with sodium cyanoborohydride. After N,N'-dialkylation with a compound of general formula III and hydrogenolytic cleavage of the aromatic protective groups, there results a compound of general formula XVII

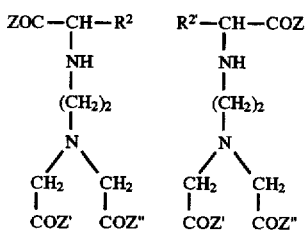

(XVII)

in which $R^2 R^{2'}$, Z, Z' and Z" have the mentioned meanings.

The compound of formula XVII is reacted in the complexing agents according to the invention with a suitable ligand, which can be obtained from a C-substituted β-amino alcohol, which first is N-alkylated with a haloacetic acid in the usual way and whose hydroxy group is converted in a way known in the art, e.g., to a bromide.

In another synthesis variant, a start is made from a substituted DTPA (diethylenetriaminepentaacetic acid) of general formula XVIII

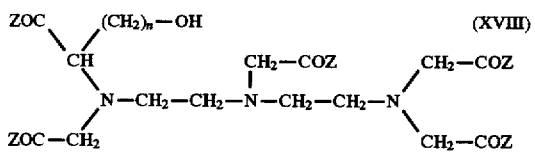

(XVIII)

in which Z and n have the above-mentioned meaning.

Such compounds can be obtained, for example, in a way known to one skilled in the art by hydrogenolytic cleavage of a benzyl ether described in Example 4b) of EP-A 0 230 893. After conversion of the hydroxyl group to a nucleofuge Nf (such as, e.g., a bromide, mesylate or tosylate), an alkylating reactant is obtained, which is reacted with a phenol of general formula XII or with an alcohol of general formula XVIII. After cleavage of optionally present protective groups, the complexing agents of general formula I with Y meaning hydrogen are obtained.

Additional compounds of general formula I are attained in that a diamino compound of general formula II, XIII or XVII is reacted with a nitroethene optionally substituted with $R^7$, $R^8$, $R^{13}$ or $R^9$, $R^{10}$, $R^{14}$ according to the type of a Michael condensation reaction, the nitro groups are reduced, for example, with samarium diiodide [M. A. Sturgess et al., Tetrahedron Lett. 34 (1993): 4743–4746] and the amino groups produced are alkylated in the usual way with a reactant of general formula IX and then optionally present protective groups are cleaved.

Compounds of general formula I containing thiol groups are attained according to the above-described process, and the thiol groups contained in the precursors generally are present in protected form and are released in one of the last reaction steps (cf. T. W. Green and P. G. M. Wuts, Protective Groups in Organic Synthesis, J. Wiley & Sons Inc., New York).

The production of the pharmaceutical agents according to the invention also takes place in a way known in the art, by the complex compounds according to the invention— optionally by the addition of the additives usual in galenicals—being suspended or dissolved in aqueous medium and then the suspension or solution optionally being sterilized. Suitable additives are, for example, physiologically harmless buffers (such as, for example, tromethamine), small additions of complexing agents (such as, for example, DTPA or the respective compound of general formula I according to the invention with Y meaning hydrogen) and/or their calcium, magnesium or zinc salts or optionally electrolytes (such as, for example, sodium chloride) as well as antioxidants (such as, for example, ascorbic acid).

If suspensions or solutions of the agents according to the invention in water or physiological salt solution are desired for enteral administration or other purposes, they are mixed with one or more adjuvant(s) usual in galenicals (for example, methylcellulose, lactose, mannitol), and/or surfactant(s) (for example, lecithins, Tween®, Myrj®) and/or flavoring substance(s) for taste correction (for example, ethereal oils).

In principle, it is also possible to produce the pharmaceutical agents according to the invention even without isolating the complex salts. In any case, special care must be used to undertake the chelation, so that the salts and salt solutions according to the invention are practically free of noncomplexed metal ions having a toxic effect.

This can be assured, for example, with the help of color indicators, such as xylenol orange, by control titrations during the production process. The invention therefore also relates to a process for the production of complex compounds and their salts. A purification of the isolated complex salt remains as a final precaution.

The pharmaceutical agents according to the invention preferably contain 1 μmol–5 mol/l of the complex salt and are generally dosed in amounts of 0.001–20 mmol/kg. They are intended for enteral and parenteral administration.

The complex compounds according to the invention are used:

1. for diagnostic radiology and NMR diagnosis in the form of their complexes with the ions of elements with atomic numbers 1–29, 42, 44 and 57–83;

2. for radiodiagnosis and radiotherapy in the form of their complexes with the radioisotopes of the elements with atomic numbers 27, 29, 31, 37–39, 43, 49, 62, 64, 70, 75, 77 and 83.

3. for neutron capture therapy.

The agents according to the invention are especially very well suited as x-ray contrast media, and it can especially be emphasized that no signs of the anaphylacticlike reactions, known from the iodine-containing contrast media, can be detected with them in biochemical-pharmacological investigations. The substances according to the invention meet the varied requirements which are to be imposed for contrast media in modern diagnosis. The compounds and agents produced from them are distinguished by a high absorption coefficient for x rays, good compatibility, which is necessary to maintain the noninvasive nature of the investigations, high effectiveness, which is necessary to load the body with the smallest possible amounts of foreign substances, good water solubility (this allows for the production of highly-concentrated solutions, as they are necessary especially for use as x-ray contrast media, thus the volume load of the circulatory system can be kept within reasonable limits), low viscosity, low osmolality, advantageous precipitation kinetics.

In addition to the surprisingly high water solubility of the optionally paramagnetic heavy metal complexes, which was able to be increased in a range necessary for diagnostic radiology, the compounds according to the invention have a positive effect in diagnostic radiology in that the complex compounds according to the invention especially also permit investigations with shorter-wave x-ray radiation than that which is possible with conventional contrast media, by which the radiation exposure of the patient is considerably reduced, since, as is generally known, soft radiation of tissue is much more greatly absorbed than hard (R. Felix, "Das R öntgenbild [The X-Ray Image]"; Thieme-Verlag Stuttgart (1980)].

Because of the advantageous absorption properties of the contrast media according to the invention in the area of hard x-ray radiation, the agents are also especially suitable for digital subtraction techniques (which work with higher tube voltages).

Details of use of x-ray contrast media are discussed, for example, in Barke, Röntgenkontrastmittel [X-Ray Contrast Media], G. Thieme, Leipzig (1970) and P. Thurn, E. B ücheler "Einführung in die Röntgendiagnostik [Introduction to Diagnostic Radiology]," G. Thieme, Stuttgart, New York (1977).

In general, the agents according to the invention for use as x-ray contrast media are dosed in amounts of 0.1–20 mmol/kg of body weight, preferably 0.25–5 mmol/kg of body weight.

The agents according to the invention, if they are paramagnetic, also meet the varied requirements for suitability as contrast media for nuclear spin tomography. Thus, after oral or parenteral administration, they are very well suited to improve the image, obtained with the aid of a nuclear spin tomograph, in its informative value by increasing the signal intensity. Further, they show the high effectiveness which is necessary to load the body with the smallest possible amounts of foreign substances and the good compatibility which is necessary to maintain the noninvasive nature of the investigations.

In general, the agents according to the invention for use as NMR diagnostic agents are dosed in amounts of 0.001–5 mmol/kg, preferably 0.005–0.5 mmol/kg. Details of use are discussed, for example, in H. J. Weinmann et al., Am. J. of Roentgenology 142, 619 (1984).

Especially low dosages (under 1 mg/kg of body weight) of organ-specific NMR diagnostic agents can be used, for example, to detect tumors and myocardial infarctions.

Further, the complex compounds according to the invention can be used advantageously as susceptibility reagents and as shift reagents for in vivo NMR spectroscopy.

If the agents according to the invention are radioactive, they are also suitable as radiodiagnostic agents because of their advantageous properties and the good stability of the complex compounds contained in them. Details of their use and dosage are described, e.g., in "Radiotracers for Medical Applications," CRC Press, Boca Raton, Fla.

Another imaging method with radioisotopes is positron emission tomography, which uses positron-emitting isotopes, such as, e.g., $^{43}$Sc, $^{44}$Sc, $^{52}$Fe, $^{55}$Co and $^{68}$Ga [Heiss, W. D.; Phelps, M. E.; Positron Emission Tomography of Brain, Springer-Verlag Berlin, Heidelberg, New York (1983)].

The compounds according to the invention can also be used in radioimmunotherapy or radiation therapy. The latter is distinguished from the corresponding diagnosis only by the amount and type of the isotope used. The object in this case is the destruction of tumor cells by high-energy short-wave radiation with a smallest possible range of action. Suitable β-emitting ions are, e.g., $^{46}$Sc, $^{47}$Sc, $^{48}$Sc, $^{72}$Ga, $^{73}$Ga and $^{90}$Y. Suitable α-emitting ions exhibiting small half-lives are, e.g., $^{211}$Bi, $^{212}$Bi, $^{213}$Bi, $^{214}$Bi, and $^{212}$Bi is preferred. A suitable photon- and electron-emitting ion is $^{158}$Gd, which can be obtained from $^{157}$Gd by neutron capture.

If the agent according to the invention is intended for use in the variant of radiation therapy proposed by R. L. Mills et al. [Nature Vol. 336, (1988), p. 787), the central ion must be derived from a Mössbauer isotope, such as, for example, $^{57}$Fe or $^{151}$Eu.

Details of use of radiotherapeutic agents are discussed, e.g., in R. W. Kozak et al., TIBTEC, October 1986, 262.

The fluorescence properties, especially of the Eu and Tb complexes according to the invention, can be used for near-infrared imaging.

The administration of aqueous x-ray and NMR contrast medium solutions can take place enterally or parenterally, namely orally, rectally, intravenously, intraarterially, intravascularly, intracutaneously, subcutaneously (lymphography), subarachnoidally (myelography), and the intravenous administration is preferred.

The agents according to the invention exhibit not only high stability in vitro, but also surprisingly high stability in vivo, so that a release or an exchange of the ions—toxic in themselves—not covalently bound to the complexes does not take place within the time in which the new contrast media are again completely excreted.

In general, it has been possible to synthesize new complexing agents, metal complexes and metal complex salts, which open up new possibilities in diagnostic and therapeutic medicine.

The examples below are used for a more detailed explanation of the object of the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. P 44 28 874.3, filed __, are hereby incorporated by reference.

EXAMPLE 1

Digadolinium complex of the tetrasodium salt of N,N,N', N'-tetrakis-{2-[N'',N''-bis-(carboxymethyl)-amino]-ethyl}-meso-2,3-diaminosuccinic acid a) N,N,N',N'-Tetrakis-{2-[N'',N''-bis-((tert-butyloxycarbonyl)-methyl)-amino]-ethyl}-meso-2,3-diaminosuccinic acid-di-tert-butyl ester 10.9 g (32.7 mmol) of meso-2,3-diaminosuccinic acid-di-tert-butyl ester-dihydrochloride (Biernat, Rosc. Chem. 43, 421 (1969)) and 51.8 g (147 mmol) of N,N-bis-[(tert-butyloxycarbonyl)-methyl]-2-bromoethylamine (M. Williams and H. Rapoport, J. Org. Chem. 58, 1151 (1993)) are introduced in 50 ml of acetonitrile and mixed with 40 ml of 2n phosphate buffer solution (pH 8.0). The batch is stirred vigorously at room temperature for 24 hours, and the aqueous phosphate buffer phase is exchanged after 2 and 8 hours for fresh buffer solution. Then, the organic phase is concentrated by evaporation in a vacuum and the residue is chromatographed on silica gel with hexane/ethyl acetate/ triethylamine (3:1:0.01). The product-containing fractions are concentrated by evaporation in a vacuum.

Yield: 35.4 g (82.3% of theory) of colorless oil.

Analysis (relative to solventless substance): Cld: C 60.69, H 9.29, N 6.24; Fnd: C 60.58, H 9.44, N 6.11.

b) N,N,N',N'-Tetrakis-{2-[N'',N''-bis-(carboxymethyl)-amino]-ethyl}-meso-2,3-diaminosuccinic acid 26.6 g (19.8 mmol) of the decaester described in Example 1a) is dissolved in 150 ml of methanol and mixed with 119 ml of 2n sodium hydroxide solution. It is refluxed for about 2 hours, the methanol is drawn off in a vacuum and stirred for another 3 hours at 60° C. Then, it is adjusted to pH 1 with concentrated hydrochloric acid, evaporated to dryness in a vacuum and the residue is absorptively precipitated with isopropanol. After filtration and concentration by evaporation of the filtrate in a vacuum, a colorless oil is obtained.

Yield: 14.0 g (90.3% of theory)

Analysis (relative to anhydrous substance): Cld: C 42.86, H 5.65, N 10.71; Fnd: C 42.92, H 5.81, N 10.57.

c) Digadolinium complex of the tetrasodium salt of N,N,N', N'-tetrakis-{2-[N",N"-bis-(carboxymethyl)-amino]-ethyl}-meso-2,3-diaminosuccinic acid 10.1 g (12.9 mmol) of the deca acid described in Example 1b) is taken up in 100 ml of water, mixed with 4.67 g (12.9 mmol) of gadolinium oxide and stirred for 3 hours at 60° C. Then, it is adjusted to pH 7.2 with diluted sodium hydroxide solution, filtered and the filtrate is freeze-dried.

Yield: 14.7 g (96.7% of theory) of colorless lyophilizate

Analysis (relative to solventless substance): Cld: C 28.47, H 2.90, Gd 26.63, N 7.12, Na 7.79; Fnd: C 28.64, H 2.98, Gd 26.53, N 7.08, Na 7.89.

EXAMPLE 2

Digadolinium complex of the tetrasodium salt of N,N,N', N'-tetrakis-{2-[N",N"-bis-(carboxymethyl)-amino]-ethyl}-meso-2,6-diaminopimelic acid a) N,N,N',N'-Tetrakis-{2-[N",N"-bis-((tert-butyloxycarbonyl)-methyl)-amino]-ethyl}-meso-2,6-diaminopimelic acid-di-tert-butyl ester 11.3 g (30.1 mmol) of meso-2,3-diaminopimelic acid-di-tert-butyl ester-dihydrochloride (Bricas et al., Bull. Soc. Chim. Fr. (1965) 1813) and 47.7 g (135 mmol) of N,N-bis-[(tert-butyloxycarbonyl)-methyl]-2-bromoethylamine (M. Williams and H. Rapoport, J. Org. Chem. 58, 1151 (1993)) are introduced in 50 ml of acetonitrile and mixed with 40 ml of 2n phosphate buffer solution (pH 8.0). The batch is stirred vigorously at room temperature for 24 hours, and the aqueous phosphate buffer phase is exchanged after 2 and 8 hours for fresh buffer solution. Then, the organic phase is concentrated by evaporation in a vacuum, and the residue is chromatographed on silica gel with hexane/ethyl acetate/triethylamine (3:1:0.01). The product-containing fractions are concentrated by evaporation in a vacuum.

Yield: 33.7 g (80.6% of theory) of colorless oil.

Analysis (relative to solventless substance): Cld: C 61.45, H 9.44, N 6.06; Fnd: C 61.54, H 9.63, N 5.92.

b) N,N,N',N'-Tetrakis-{2-[N",N"-bis-(carboxymethyl)-amino]-ethyl}-meso-2,3-diaminopimelic acid 30.6 g (22.0 mmol) of the decaester described in Example 2a) is dissolved in 150 ml of methanol and mixed with 132 ml of 2n sodium hydroxide solution. It is refluxed for about 2 hours, the methanol is drawn off in a vacuum and stirred for another 3 hours at 60° C. Then, it is adjusted to pH 1 with concentrated hydrochloric acid, evaporated to dryness in a vacuum and the residue is absorptively precipitated with isopropanol. After filtration and concentration by evaporation of the filtrate in a vacuum, a colorless oil is obtained.

Yield: 17.3 g (94.8% of theory)

Analysis (relative to hydrochloric acid-free substance): Cld: C 45.04, H 6.10, N 10.17; Fnd: C 44.95, H 5.92, N 10.20.

c) Digadolinium complex of the tetrasodium salt of N,N,N', N'-tetrakis-{2-[N",N"-bis-(carboxymethyl)-amino]-ethyl}-meso-2,6-diaminopimelic acid 15.4 g (18.6 mmol) of the deca acid described in Example 2b) is taken up in 100 ml of water, mixed with 6.75 g (18.6 mmol) of gadolinium oxide and stirred for 3 hours at 60° C. Then, it is adjusted to pH 7.2 with diluted sodium hydroxide solution, filtered and the filtrate is freeze-dried. Yield: 20.3 g (89.3% of theory) of colorless lyophilizate Analysis (relative to solventless substance): Cld: C 30.44, H 3.30, Gd 25.71, N 6.87, Na 7.52; Fnd: C 30.41, H 3.41, Gd 25.66, N 6.93, Na 7.48.

EXAMPLE 3

Diytterbium complex of the tetrasodium salt of 3-{4-[2-[N,N-bis-[2-[N',N'-bis-(carboxymethyl)-amino]ethyl]]-amino-2-carboxyethyl]-phenoxy}-2-N-{2-[N'-[2-[N",N"-bis-(carboxymethyl)-amino]-ethyl]-N'-(carboxymethyl)-amino]-ethyl}-N-(carboxymethyl)-amino}-propionic acid a) 3-{4-[2-[N,N-bis-[2-N',N'-bis-(benzyloxycarbonylmethyl)-amino]-ethyl]]-amino-2-(benzyloxycarbonyl)-ethyl)]-phenoxy}-2-{N-{2-[N'-[2-[N",N"-bis-(tert-butoxycarbonylmethyl)-amino]-ethyl]]-N'-(tert-butoxycarbonylmethyl)-amino]-ethyl}-N-(tert-butoxycarbonylmethyl)-amino}-propionic acid-tert-butyl ester 10.15 g (10.7 mmol) of the compound produced according to Example 5a) is dissolved in 50 ml of anhydrous N,N-dimethylformamide and mixed at 0° C. under argon with 0.47 g (11.75 mmol) of sodium hydride suspension (60% in oil). The batch is allowed to stir for 15 minutes, and then 9.18 g (10.7 mmol) of the tosylate of Example 7c) is added. When the reaction mixture has reached room temperature, stirring is allowed to continue for 7 more hours. For working-up, the batch is taken up in toluene and shaken out several times from aqueous sodium bicarbonate solution. The organic phase is separated, dried on magnesium sulfate, filtered and concentrated by evaporation. The oily residue is chromatographed on silica gel with hexane/diethyl ether/triethylamine (30:80:1), the product-containing fractions are combined and concentrated by evaporation.

Yield: 12.8 g (73.1% of theory) of pale yellow oil.

Analysis (taking into consideration the solvent content): Cld: C 66.81, H 7.52, N 5.14; Fnd: C 66.68, H 7.70, N 5.21.

b) 3-{4-[2-[(N,N-bis-[2-[N',N'-bis-(carboxymethyl)-amino]-ethyl]]-amino-2-carboxyethyl]-phenoxy}-2-{N-{2-[N'-[2-[N",N"-bis-(carboxymethyl)-amino]-ethyl]-N'-(carboxymethyl)-amino]-ethyl}-N-(carboxymethyl)-amino}-propionic acid 12.5 g (7.6 mmol) of the decaester described in Example 3a) is dissolved in 110 ml of methanol and mixed with 105 ml of 2n sodium hydroxide solution. It is refluxed for about 3.5 hours, the methanol is drawn off in a vacuum and stirred for another 4 hours at 60° C. Then, it is adjusted to pH 1 with concentrated hydrochloric acid, evaporated to dryness in a vacuum and the residue is absorptively precipitated with ethanol. After filtration and concentration by evaporation of the filtrate in a vacuum, a colorless solid is obtained.

Yield: 6.2 g (90% of theory)

Analysis (taking into consideration the solvent content): Cld: C 47.79, H 5.79, N 9.29; Fnd: C 47.87, H 5.80, N 9.14.

c) Diytterbium complex of the tetrasodium salt of 3-{4-[2-[N,N-bis-[2-[N',N'-bis-(carboxymethyl)-amino]-ethyl]]-amino-2-carboxyethyl]-phenoxy}-2-{N-{2-[N'-[2-N",N"-bis-(carboxymethyl)-amino]-ethyl]-N'-(carboxymethyl)-amino]-ethyl}-N-(carboxymethyl)-amino}-propionic acid 5.9 g (6.5 mmol) of the deca acid of Example 3b) is taken up in 90 ml of water, mixed with 1.28 g (3.25 mmol) of ytterbium oxide and stirred for 8 hours at 65° C. Then, it is adjusted to pH 7.2 with diluted sodium hydroxide solution, filtered and the filtrate is freeze-dried.

Yield: 7.9 g (91.2% of theory) of colorless lyophilizate.

Analysis (relative to solventless substance): Cld: C 32.44, H 3.18 Yb 25.97, N 6.31, Na 6.90; Fnd: C 32.28, H 3.40 Yb 25.78, N 6.21, Na 6.73.

EXAMPLE 4

Digadolinium complex of the disodium salt of N,N,N',N'-tetrakis-{2-[N",N"-bis-(carboxymethyl)-amino]-ethyl}-meso-2,3-diaminosuccinic acid-N"',N""-bis-(2-methoxyethyl)-diamide a) meso-2,3-Diaminosuccinic acid-N,N'-bis-(2-methoxyethyl)-diamide, diacetate A suspension of 13.9 g (50.1 mmol) of meso-2,3-diaminosuccinic acid-diethyl ester-dihydrochloride (Tamura, J. Biochem. Tokyo 27 [1938]339) in 50 ml of ethanol is mixed with 38.7 g (0.51 mmol) of 2-methoxyethylamine and refluxed for 12 hours. Then, it is completely concentrated by evaporation and the residue is chromatographed on silica gel with dichloromethane/methanol/acetic acid. After the concentration by evaporation of the product-containing fractions, a slightly yellowish oil is obtained.

Yield: 17.2 g (88.2% of theory)

Analysis: Cld: C 43.97, H 7.91, N 14.96; Fnd: C 44.04, H 8.01, N 14.83.

b) N,N,N',N'-Tetrakis-{2-[N",N"-bis-((benzyloxycarbonyl)-methyl)-amino]-ethyl}-meso-2,3-diaminosuccinic acid-N"', N""-bis-(2-methoxyethyl)-diamide 14.2 g (37.1 mmol) of the compound produced according to Example 4a) and 70.2 g (167 mmol) of N,N-bis-[(benzyloxycarbonyl)-methyl]-2-bromoethylamine (M. Williams and H. Rapoport, J. Org. Chem. 58, 1151 (1993)) are introduced in 70 ml of acetonitrile and mixed with 60 ml of 2n phosphate buffer solution (pH 8.0). The batch is stirred vigorously at room temperature for 24 hours, and the aqueous phosphate buffer phase is exchanged after 2 and 8 hours for fresh buffer solution. Then, the organic phase is concentrated by evaporation in a vacuum and the residue is chromatographed on silica gel with hexane/ethyl acetate/triethylamine (3:1:0.01). The product-containing fractions are concentrated by evaporation in a vacuum.

Yield: 46.6 g (77.3% of theory) of colorless oil.

Analysis (relative to solventless substance): Cld: C 66.73, H 6.60, N 6.92; Fnd: C 66.59, H 6.65, N 6.87.

c) N,N,N',N'-Tetrakis-{2-[N",N"-bis-(carboxymethyl)-amino]-ethyl}-meso-2,3-diaminosuccinic acid-N"',N""-bis-(2-methoxyethyl)-diamide 33.6 g (20.7 mmol) of the decaester described in Example 4b) is dissolved in 150 ml of methanol and mixed with 104 ml of 2n sodium hydroxide solution. It is refluxed for about 2 hours, the methanol is drawn off in a vacuum and stirred for another 3 hours at 60° C. Then, it is adjusted to pH 1 with concentrated hydrochloric acid, evaporated to dryness in a vacuum and the residue is absorptively precipitated with isopropanol. After filtration and concentration by evaporation of the filtrate in a vacuum, a colorless oil is obtained.

Yield: 17.4 g (93.4% of theory)

Analysis (relative to hydrochloric acid-free substance): Cld: C 45.43, H 6.50, N 12.47; Fnd: C 45.35, H 6.61, N 12.34.

d) Digadolinium complex of the disodium salt of N,N,N',N'-tetrakis-{2-[N",N"-bis-(carboxymethyl)-amino]-ethyl}-meso-2,3-diaminosuccinic acid-N"',N""-bis-(2-methoxyethyl)-diamide 16.8 g (18.7 mmol) of the octa acid described in Example 4c) is taken up in 150 ml of water, mixed with 6.78 g (18.7 mmol) of gadolinium oxide and stirred for 3 hours at 80° C.

Then, it is adjusted to pH 7.2 with diluted sodium hydroxide solution, filterd and the filtrate is freeze-dried.

Yield: 22.3 g (95.3% of theory) of colorless lyophilizate

Analysis (relative to solventless substance): Cld: C 32.64, H 4.03, N 8.95, Gd 25.13, Na 3.68; Fnd: C 32.65, H 4.09, N 9.04, Gd 25.06, Na 3.59.

EXAMPLE 5

Digadolinium complex of the tetrasodium salt of 1,8-bis-{4-[2-(N,N-bis-(2-(N',N'-bis-(carboxymethyl)-amino)-ethyl)-amino)-2-carboxyethyl]-phenoxy}-octane a) N,N-Bis-{2-[N',N'-bis-[(benzyloxycarbonyl)-methyl]-amino]-ethyl}-L-tyrosine benzyl ester 15.5 g (35.0 mmol) of L-tyrosine benzyl ester-4-methylbenzensulfonate and 66.2 g (158 mmol) of N,N-bis-[(benzyloxycarbonyl)-methyl]-2-bromoethylamine (M. Williams and H. Rapoport, J. Org. Chem. 58, 1151 (1993)) are introduced in 70 ml of acetonitrile and mixed with 60 ml of 2n phosphate buffer solution (pH 8.0). The batch is stirred vigorously at room temperature for 24 hours, and the aqueous phosphate buffer phase is exchanged after 2 and 8 hours for fresh buffer solution. Then, the organic phase is concentrated by evaporation in a vacuum, and the residue is chromatographed on silica gel with hexane/ethyl acetate/triethylamine (3:1:0.01). The product-containing fractions are concentrated by evaporation in a vacuum.

Yield: 23.4 g (70.3% of theory) of colorless oil.

Analysis (relative to solventless substance): Cld: C 70.79, H 6.26, N 4.42; Fnd: C 70.69, H 6.33, N 4.51.

b) 1,8-Bis-{4-[2-(N,N-bis-(2-(N',N'-bis-((benzyloxycarbonyl)-methyl)-amino)-ethyl)-amino)-2-(benzyloxycarbonyl)-ethyl]-phenoxy}-octane 20.3 g (21.4 mmol) of the compound produced according to Example 5a) is dissolved in 50 ml of anhydrous N,N-dimethylformamide and mixed at 0° C. under argon with 0.94 g (23.5 mmol) of sodium hydride suspension (60% in oil). The batch is allowed to stir for 15 minutes and then 3.91 g (10.7 mmol) of 1,8-diiodooctane is added. When the reaction mixture has reached room temperature, stirring is allowed to continue for 5 more hours. For working-up, the batch is taken up in toluene and shaken out several times from aqueous sodium bicarbonate solution. The organic phase is separated, dried on magnesium sulfate, filtered and concentrated by evaporation. The oily residue is chromatographed on silica gel with hexane/diethyl ether/triethylamine (30:80:1), the product-containing fractions are combined and concentrated by evaporation. Yield: 15.3 g (71.1% of theory) of colorless oil Analysis (relative to solventless substance): Cld: C 71.69, H 6.62, N 4.18; Fnd: C 71.53, H 6.78, N 4.07.

c) 1,8-bis-{4-[2-(N,N-bis-(2-(N',N'-bis-(carboxymethyl)-amino)-ethyl)-amino)-2-carboxyethyl]-phenoxy}-octane 14.5 g (7.21 mmol) of the decaester described in Example 5b) is dissolved in 145 ml of methanol and after the addition of 1.4 g of palladium (10%) on activated carbon, it is hydrogenated under hydrogen atmosphere until hydrogen absorption is completed. After filtration and concentration by evaporation of the filtrate in a vacuum, a colorless oil is obtained.

Yield: 7.95 g (99.4% of theory)

Analysis (relative to solventless substance): Cld: C 54.15, H 6.54, N 7.58; Fnd: C 54.00, H 6.62, N 7.47.

d) Digadolinium complex of the tetrasodium salt of 1,8-bis-{4-[2-(N,N-bis-(2-(N',N'-bis-(carboxymethyl)-amino)-ethyl)-amino)-2-carboxyethyl]-phenoxy}-octane 7.87 g (7.10 mmol) of the deca acid described in Example 5c) is taken up in 25 ml of water, mixed with 2.57 g (7.10 mmol) of gadolinium oxide and stirred for 3 hours at 60° C. Then, it is adjusted to pH 7.2 with diluted sodium hydroxide solution, filtered and the filtrate is freeze-dried.

Yield: 10.5 g (98.6% of theory) of colorless lyophilizate

Analysis (relative to solventless substance): Cld: C 39.89, H 4.15, Gd 20.89, N 5.58, Na 6.11; Fnd: C 39.88, H 4.23, Gd 20.78, N 5.62, Na 6.18.

EXAMPLE 6

Didysprosium complex of the tetrasodium salt of N,N'-bis-{2-[N",N"-bis-(carboxymethyl)-amino]-3-[(4-methoxy)-phenyl]-propyl}-N,N'-bis-{2-[N''',N'''-bis-(carboxymethyl)-amino]-ethyl}-meso-2,3-diaminosuccinic acid a) N,N'-Dibenzyl-meso-2,3-diaminosuccinic acid-di-tert-butyl ester 11.9 g (35.7 mmol) of meso-2,3-diaminosuccinic acid-di-tert-butyl ester-dihydrochloride (Biernat, Rosc. Chem. 43, 421 (1969)) and 8.33 g (78.6 mmol) of benzaldehyde are stirred in 50 ml of methanol for 3 hours at 24° C. and then mixed with 3.37 g (53.6 mmol) of sodium cyanoborohydride. After 48 hours of stirring at room temperature, the batch is adjusted to pH 2 by careful addition of semiconcentrated hydrochloric acid, then neutralized with concentrated aqueous sodium bicarbonate solution and after substantial evaporation of methanol, it is shaken out with ethyl acetate. The organic phase is dried on anhydrous magnesium sulfate, filtered and concentrated by evaporation. The residue is chromatographed on silica gel with diethyl ether/hexane/triethylamine (70:30:1); the product-containing fractions are combined and concentrated by evaporation.

Yield: 9.69 g (61.1% of theory) of colorless oil

Analysis (relative to solventless substance): Cld: C 70.88, H 8.24, N 6.36; Fnd: C 70.72, H 8.33, N 6.41.

b) N,N'-Dibenzyl-N,N'-bis-{2-[N",N"-bis-((tert-butyloxycarbonyl)-methyl)-amino]-ethyl}-meso-2,3-diaminosuccinic acid-di-tert-butyl ester 9.21 g (20.9 mmol) of the compound produced according to Example 6a) and 10.2 g (52.3 mmol) of N,N-bis-[(tert-butyloxycarbonyl)-methyl]-2-bromoethylamine (M. Williams and H. Rapoport, J. Org. Chem. 58, 1151 (1993)) are introduced in 30 ml of acetonitrile and mixed with 20 ml of 2n phosphate buffer solution (pH 8.0). The batch is vigorously stirred at room temperature for 24 hours, and the aqueous phosphate buffer phase is exchanged after 2 and 8 hours for fresh buffer solution. Then, the organic phase is concentrated by evaporation in a vacuum, and the residue is chromatographed on silica gel with hexane/ethyl acetate/triethylamine (3:1:0.01) The product-containing fractions are concentrated by evaporation in a vacuum.

Yield: 16.2 g (78.9% of theory) of colorless oil

Analysis (relative to solventless substance): Cld: C 65.96, H 8.82, N 5.70; Fnd: C 66.07, H 8.74, N 5.77.

c) N,N'-Bis-{2-[N",N"-bis-((tert-butyloxycarbonyl)-methyl)-amino]-ethyl}-meso-2,3-diaminosuccinic acid-di-tert-butyl ester 15.3 g (15.6 mmol) of the compound produced according to Example 6b) is dissolved in 75 ml of ethanol and after the addition of 1.5 g of palladium (10%) on activated carbon under hydrogen atmosphere, it is hydrogenated at room temperature until hydrogen absorption is completed. After filtration and concentration by evaporation of the filtrate in a vacuum, a colorless oil is obtained.

Yield: 12.5 g (100% of theory)

Analysis: Cld: C 59.83, H 9.29, N 6.98; Fnd: C 59.96, H 9.15, N 6.88.

d) 2-[N,N-Bis-((tert-butyloxycarbonyl)-methyl)-amino]-3-[(4-methoxy)-phenyl]-propanol 18.1 g (100 mmol) of 2-amino-3-[(4-methoxy)-phenyl]-propanol (L. Berlinguet, Can. J. Chem. 32, 31 (1954)) is dissolved in 100 ml of tetrahydrofuran and mixed with 10 ml of water and 20.7 g (150 mmol) of potassium carbonate. After instillation of 42.9 g (220 mmol) of bromoacetic acid-tert-butyl ester, it is stirred for 3 days at 60° C. After the cooling, it is filtered, concentrated by evaporation in a vacuum, and the residue is chromatographed on silica gel with diethyl ether/hexane/triethylamine (70:20:5). The product fractions are concentrated by evaporation in a vacuum and dried.

Yield: 36.7 g (89.6% of theory) of colorless oil

Analysis (relative to solventless substance): Cld: C 64.52, H 8.61, N 3.42; Fnd: C 64.55, H 8.50, N 3.51.

e) 1-Bromo-2-[N,N-bis-((tert-butyloxycarbonyl)-methyl)-amino]-3-[(4-methoxy)-phenyl]-propane A solution of 35.8 g (75.8 mmol) and 22.9 g (87.1 mmol) of triphenylphosphine in 400 ml of dichloromethane is mixed at 0° C. in portions with 15.5 g (87.1 mmol) of N-bromosuccinimide and then stirred overnight at room temperature. The solution is concentrated by evaporation and the residue is pulverized with tert-butyl methyl ether. A precipitate develops, which is separated and washed with tert-butyl methyl ether. The combined filtrates are concentrated by evaporation, and the residue is chromatographed on silica gel with hexane/diethyl ether (2:1). Concentration by evaporation of the product fractions yields a colorless oil.

Yield: 32.6 g (91.0% of theory)

Analysis: Cld: C 55.93, H 7.25, Br 16.91, N 2.97; Fnd: C 56.12, H 7.26, Br 16.97, N 2.83.

f) N,N'-Bis-{2-[N",N"-bis((tert-butyloxycarbonyl)-methyl)-amino]-3-[(4-methoxy)-phenyl]-propyl}-N,N'-bis-{2-{N''',N'''-bis-((tert-butyloxycarbonyl)-methyl)-amino]-ethyl}-meso-2,3-diaminosuccinic acid-di-tert-butyl ester 8.34 g (10.4 mmol) of the compound produced according to Example 6c) and 10.8 g (22.8 mmol) of the compound produced according to Example 6e) are introduced in 20 ml of acetonitrile and mixed with 15 ml of 2n phosphate buffer solution (pH 8.0). The batch is stirred vigorously at room temperature for 24 hours, and the aqueous phosphate buffer phase is exchanged after 2 and 8 hours for fresh buffer solution. Then, the organic phase is concentrated by evaporation in a vacuum and the residue is chromatographed on silica gel with hexane/ethyl acetate/triethylamine (3:1:0.01). The product-containing fractions are concentrated by evaporation in a vacuum. Yield: 10.8 g (65.6% of theory) of colorless oil Analysis (relative to solventless substance): Cld: C 51.56, H 5.90, N 8.20; Fnd: C 51.49, H 6.01, N 8.33.

g) N,N'-Bis-{2-[N",N"-bis-(carboxymethyl)-amino]-3-[(4-methoxy)-phenyl]-propyl}-N,N'-bis-{2-[N''',N'''-bis-(carboxymethyl)-amino]-ethyl}-meso-2,3-diaminosuccinic acid 10.1 g (6.36 mmol) of the compound produced according to Example 6f) is dissolved in 20 ml of methanol and mixed with stirring drop by drop with 80 ml of semiconcentrated hydrochloric acid. After 3 hours of stirring at room temperature, it is concentrated by evaporation in a vacuum and dried.

Yield: 6.53 g (100% of theory) of colorless oil

Analysis (relative to hydrochloric acid-free substance): Cld: C 51.56, H 5.90, N 8.20; Fnd: C 51.67, H 5.95, N 8.11.

h) Didysprosium complex of tetrasodium salt of N,N'-bis-{2-[N",N"-bis-(carboxymethyl)-amino]-3-[(4-methoxy)-phenyl]-propyl}-N,N'-bis-{2-[N''',N'''-bis-(carboxymethyl)-amino]-ethyl}-meso-2,3-diaminosuccinic acid 5.95 g (5.80 mmol) of the deca acid described in Example 6g) is taken up in 20 ml of water, mixed with 2.17 g (5.80 mmol) of dysprosium oxide and stirred for 3 hours at 60° C. Then, it is adjusted to pH 7.2 with diluted sodium hydroxide solution, filtered and the filtrate is freeze-dried.

Yield: 7.76 g (93.4% of theory) of colorless lyophilizate

Analysis (relative to solventless substance): Cld: C 36.91, H 3.52, Dy 22.70, N 5.87, Na 6.42; Fnd: C 37.10, H 3.55, Dy 22.59, N 5.92, Na 6.38.

EXAMPLE 7

Digadolinium complex of the tetrasodium salt of 3,6,9,15, 18,21-hexaaza-10,14-bis-carboxy-3,6,9,15,18,21-hexakis-(carboxymethyl)-12-oxa-tricosane-1,23-dioic acid a) 3-(Phenylmethoxy)-2{-N-{2-[N'-[2-[N",N"-bis-(tert-butyloxycarbonylmethyl)-amino]-ethyl]]-N'-(tert-butyloxycarbonylmethyl)-amino]-ethyl}-N-(tert-butyloxycarbonylmethyl)-amino}-propionic acid 5.13 g (10 mmol) of 3-phenylmethoxy-2-N-{2'-N'-[2"-N",N"-bis-(carboxymethyl)-aminoethyl]-N'-(carboxymethyl)-aminoethyl]-N'-(carboxymethyl)-aminopropionic acid (Example 4B of EP 230 893) is mixed in 60 ml of tert-butyl acetate with 0.8 ml (9 mmol) of perchloric acid (70%) at room temperature and stirred for 3 days. After completion of the reaction, the batch is poured on ice/water and the acid is neutralized. It is extracted several times with diethyl ether, the organic phase is dried on sodium sulfate, filtered and the ether is evaporated. The residue is chromatographed on silica gel.

Yield: 5.4 g (68% of theory) of colorless oil.

Analysis (taking into consideration the solvent content): Cld: C 63.53, H 9.01, N 5.29; Fnd: C 63.29, H 9.24, N 5.24.

b) 3-Hydroxy-2-{N-{2-[N'-[2-[N",N"-bis-(tert-butyloxycarbonylmethyl)-amino]-ethyl]-N'-(tert-butyloxycarbonylmethyl)-amino]-ethyl}-N-(tert-butyloxycarbonylmethyl)-amino}-propionic acid 4.95 g (6.2 mmol) of the benzyl ether of Example 7a) is dissolved in 30 ml of methanol and after the addition of 1.4 g palladium (10%) on activated carbon under hydrogen atmosphere, it is hydrogenated at room temperature until hydrogen absorption is completed. After filtration and concentration by evaporation of the filtrate in a vacuum, a colorless oil is obtained.

Yield: 4.1 g (94% of theory).

Analysis (taking into consideration the solvent content): Cld: C 59.72, H 9.31, N 5.97; Fnd: C 59.65, H 9.14, N 6.11.

c) 3-(4-Methylbenzenesulfonyloxy)-2-{N-{2-[N'-[2-[N",N"-bis-(tert-butyloxycarbonylmethyl)-amino]-ethyl]-N'-(tert-butyloxycarbonylmethyl)-amino]-ethyl]-N-(tert-butyloxycarbonylmethyl)-amino}propionic acid 3.8 g (5.4 mmol) of the alcohol of Example 7b) is stirred in 40 ml of dichloromethane and 0.84 ml (6.5 mmol) of triethylamine at 0° C. under nitrogen and mixed drop by drop with 1.13 g (6 mmol) of methanesulfonic acid chloride. The reaction temperature is allowed to increase to room temperature within 3 hours, and the batch is shaken out with saturated sodium bicarbonate solution. The organic phase is dried on sodium sulfate, filtered and concentrated by evaporation.

Yield: 3.5 g (75.5% of theory) of pale yellowish oil

Analysis (relative to solventless substance): Cld: C 58.79, H 8.34, N 4.90, S 3.74; Fnd: C 58.63, H 8.51, N 4.73, S 3.60.

d) 3,6,9,15,18,21-Hexaaza-10,14-bis-(tert-butyloxycarbonyl)-3,6,9,15,18,21-hexakis-(tert-butyloxycarbonylmethyl)-12-oxa-tricosane-1,23-dioic acid-di-tert-butyl ester A solution of 5.36 g (7.61 mmol) of the alcohol, produced according to Example 7b), in 20 ml of anhydrous N,N-dimethylformamide is mixed at 0° C. with 0.33 g (8.25 mmol) of sodium hydride (60% in oil) and stirred for 15 minutes under argon. Then, 6.53 g (7.61 mmol) of the tosylate produced according to Example 7c) and 0.13 g (0.76 mmol) of potassium iodide are added and the reaction mixture is stirred for one hour at 0° C. and for eight hours at room temperature. For working-up, the reaction mixture is taken up in 100 ml of ethyl acetate and shaken out from aqueous sodium bicarbonate solution. The organic phase is dried, filtered and concentrated by evaporation on sodium sulfate. The residue is chromatographed on silica gel and the product-containing fractions are combined and concentrated by evaporation in a vacuum.

Yield: 6.7 g (63.3% of theory) of colorless oil.

Elementary analysis (taking into consideration the solvent content): Cld: C 60.50, H 9.28, N 6.05; Fnd: C 60.38, H 9.33, N 6.21.

e) Digadolinium complex of the tetrasodium salt of 3,6,9, 15,18,21-hexaaza-10,14-bis-carboxy-3,6,9,15,18,21-hexakis-(carboxymethyl)-12-oxa-tricosane-1,23-dioic acid 6.65 g (4.8 mmol) of the decaester described in Example 7d) is dissolved in 40 ml of methanol and mixed with 30 ml of 2n sodium hydroxide solution. It is refluxed for about 3 hours, the methanol is drawn off in a vacuum and stirred for another 3 hours at 60° c. Then, it is adjusted to pH 1 with concentrated hydrochloric acid, evaporated to dryness in a vacuum, and the residue is absorptively precipitated with ethanol. After filtration and concentration by evaporation of the filtrate in a vacuum, a colorless solid is obtained, which is suspended in water and complexed according to Example 1c) to ligands with gadolinium oxide. After complexing has been completed, the pH is adjusted to 7.3 with 2n sodium hydroxide solution and the aqueous solution is freeze-dried.

Yield: 5.2 g (88.4% of theory) of colorless lyophilizate.

Analysis (relative to solventless substance): Cld: C 29.41, H 3.13, Gd 25.67, N 6.86, Na 7.51; Fnd: C 29.34, H 3.41, Gd 25.59, N 6.64, Na 7.24.

EXAMPLE 8

Didysprosium complex of N,N,N',N'-tetrakis-{2-[[N"-(carboxymethyl)]-N"-((N"'-methyl)-carbamoylmethyl)-amino]-ethyl}-meso-2,6-diaminopimelic acid a) N,N,N',N'-Tetrakis-[2-(2,6-dioxomorpholino)-ethyl]-meso-2,6-diaminopimelic acid 8.27 g (10.0 mmol) of the deca acid produced according to Example 1b) is refluxed in 50 ml of acetic anhydride with exclusion of moisture for 5 hours. Following this, it is completely concentrated by evaporation and the residue is dried on an oil pump vacuum.

Yield: 75.5 g (100% of theory) of colorless oil

Analysis: Cld: C 49.34, H 5.61, N 11.14; Fnd: C 49.44, H 5.75, N 11.06.

b) N,N,N',N'-Tetrakis-{2-[[N"-(carboxymethyl)]-N"-((N"'-methyl)-carbamoylmethyl)-amino]-ethyl}-meso-2,6-diaminopimelic acid Gaseous methylamine is introduced into a solution of 7.43 g (9.84 mmol) of the compound, prepared according to Example 8a), in anhydrous tetrahydrofuran at 0° C. until the solution is saturated. Then, stirring of the batch is allowed to continue for 2 hours at room temperature, then it is concentrated by evaporation in a vacuum, and the residue is dried on an oil pump vacuum.

Yield: 8.65 g (100% of theory) of yellowish oil

Analysis: Cld: C 47.83, H 7.11, N 15.94; Fnd: C 47.97, H 7.24, N 16.10.

c) Didysprosium complex of N,N,N',N'-tetrakis-{2-[[N"-(carboxymethyl)]-N"-((N"'-methyl)-carbamoylmethyl)-amino]-ethyl}-meso-2,6-diaminopimelic acid 8.51 g (9.69 mmol) of the tetraamide produced according to Example 8b) is dissolved in 30 ml of water and mixed with 3.61 g (9.69 mmol) of dysprosium oxide. The solution is heated to 80° C. while a solution is present, which is completely desalinated with a little acid and basic ion exchanger, then filtered and freeze-dried.

Yield: 11.24 g (96.9% of theory) of colorless lyophilizate

Analysis (relative to anhydrous substance): Cld: C 35.09, H 4.71, N 11.69, Dy 27.13; Fnd: C 35.18, H 4.81, N 11.78, Dy 27.04.

EXAMPLE 9

Digadolinium complex of the tetrasodium salt of N,N,N',N'-tetrakis-{2-[N",N"-bis-(carboxymethyl)-amino]-2-(hydroxymethyl)-propyl}-meso-2,3-diaminosuccinic acid a) 2,4-Dimethyl-4-bromomethyl-2-oxazoline A solution of 40.1 g (310 mmol) of 2,4-dimethyl-4-hydroxymethyl-2-oxazoline (J. Nys and J. Libeer, Bull. Soco Chim. Belg., 65, 377 (1956)) and 85.5 g (326 mmol) of triphenylphosphine in 400 ml of dichloromethane is mixed at 0° C. in portions with 58.0 g (326 mmol) of N-bromosuccinimide and then stirred overnight at room temperature. The solution is concentrated by evaporation and the residue is pulverized with tert-butyl methyl ether. A precipitate develops, which is separated and washed with tert-butyl methyl ether. The combined filtrates are subjected to a fractionated distillation at normal pressure, and first the solvent is drawn off and then the title compound is distilled at an oil bath temperature of 200° C.

Yield: 53.2 g (89.3% of theory) of colorless oil

Analysis: Cld: C 37.52, H 5.25, Br 41.60, N 7.29; Fnd: C 37.49, H 5.31, Br 41.50, N 7.34.

b) N,N,N',N'-Tetrakis-[(2,4-dimethyl-4,5-dihydrooxazol-4-yl)-methyl]-meso-2,3-diaminosuccinic acid 11.6 g (78.3 mmol) of meso-2,3-diaminosuccinic acid and 72.2 g (375 mmol) of the bromide produced according to Example 9a) are introduced in a suspension of 80 ml of tetrahydrofuran and 40 ml of 2n phosphate buffer solution (pH 8.0) and stirred vigorously at room temperature for 24 hours, and the pH of the aqueous phosphate buffer phase is adjusted to the initial value after 2 and 8 hours. Then, the pH of the aqueous phase is lowered to 2 with semiconcentrated hydrochloric acid, the organic phase is separated and concentrated by evaporation in a vacuum. The oily residue is dried on an oil pump vacuum at 50° C. and further reacted without further purification.

Yield: 47.8 g of crude product c) N,N,N',N'-Tetrakis-[(2-amino-3-hydroxy-2-methyl)-propyl]-meso-2,3-diaminosuccinic acid-hexahydrochloride 47.8 g of the crude tetraoxazoline derivative produced according to Example 9b) is taken up in 150 ml of methanol and mixed with 50 ml of concentrated hydrochloric acid. The reaction mixture is refluxed for 3 hours and then evaporated to dryness. The residue is further reacted without purification.

Yield: 57.4 g of crude product d) N,N,N',N'-Tetrakis-[(2-amino-3-hydroxy-2-methyl)-propyl]-meso-2,3-diaminosuccinic acid-dibenzyl ester-hexa-p-toluenesulfonate 57.4 g of the crude hexahydrochloride produced according to Example 9c), 65.6 g (345 mmol) of p-toluenesulfonic acid and 84.7 g (783 mmol) of benzyl alcohol are refluxed in 300 ml of 1,2-dichloroethane in a water separator for 1 day. The precipitate formed is separated, washed with diethyl ether and dried in a vacuum. The crude product is further reacted without purification.

Yield: 135.4 g e) N,N,N',N'-Tetrakis-{2-[N",N"-bis-((benzyloxycarbonyl)-methyl)-amino]-2-(hydroxymethyl)-propyl}-meso-2,3-diaminosuccinic acid-dibenzyl ester 60.0 g (about 35 mmol) of the crude p-toluenesulfonate produced according to Example 9d) and 79.0 g (345 mmol) of bromoacetic acid benzyl ester are introduced in 100 ml of tetrahydrofuran and mixed with 71.7 (517 mmol) of triethylamine. The batch is stirred at room temperature for 24 hours at 60° C., then concentrated by evaporation, taken up in ethyl acetate and shaken out from concentrated, aqueous sodium bicarbonate solution. The organic phase is dried on magnesium sulfate, concentrated by evaporation in a vacuum and the residue is chromatographed on silica gel with hexane/ethyl acetate/triethylamine (3:1:0.01). The product-containing fractions are concentrated by evaporation in a vacuum.

Yield: 27.0 g (42.1% of theory over 4 stages) of colorless oil.

Analysis (relative to solventless substance): Cld: C 68.37, H 6.50, N 4.51; Fnd: C 68.41, H 6.55, N 4.48.

f) N,N,N',N'-Tetrakis-{2-[N",N"-bis-(carboxymethyl)-amino]-2-(hydroxymethyl)-propyl}-meso-2,3-diaminosuccinic acid 25.8 g (13.8 mmol) of the benzyl ether of Example 9e) is dissolved in 150 ml of methanol and after the addition of 2.6 g of palladium (10%) on activated carbon under hydrogen atmosphere, it is hydrogenated at room temperature until hydrogen absorption is completed. After filtration and concentration by evaporation of the filtrate in a vacuum, a colorless oil is obtained.

Yield: 13.3 g (100.0% of theory)

Analysis: Cld: C 45.00, H 6.50, N 8.75; Fnd: C 45.12, H 6.61, N 8.69.

g) Digadolinium complex of the tetrasodium salt of N,N,N',N'-tetrakis-{2-[N",N"-bis-(carboxymethyl)-amino]-2-(hydroxymethyl)-propyl}-meso-2,3-diaminosuccinic acid 10.5 g (10.9 mmol) of the deca acid described in Example 9f) is taken up in 100 ml of water, mixed with 3.96 g (12.9 mmol) of gadolinium oxide and stirred for 3 hours at 60° C. Then, it is adjusted to pH 7.2 with diluted sodium hydroxide solution, filtered and the filtrate is freeze-dried.

Yield: 14.4 g (97.4% of theory) of colorless lyophilizate

Analysis (relative to anhydrous substance): Cld: C 31.86, H 3.71, Gd 23.17, N 6.19, Na 6.78; Fnd: C 31.95, H 3.84, Gd 23.05, N 6.22, Na 6.63.

EXAMPLE 10

Digadolinium complex of the disodium salt of 3,6,11,14-tetraaza-3,14-bis-(carboxymethyl)-6,11-bis-[2-(N,N-bis-(carboxymethyl)-amino)-ethyl]-8,9-dihydroxy-hexadecane-1,16-dioic acid a) 4,5-Bis-{N,N,N',N'-tetrakis-[2-[(N",N"-bis(-tert-butyloxycarbonylmethyl))-amino]-ethyl]-aminomethyl}-2,2-dimethyl-1,3-dioxolan 8.05 g (50.2 mmol) of 4,5-bis-(aminomethyl)-2,2-dimethyl-1,3-dioxolan and 79.3 g (225 mmol) of N,N-bis-[tert-butyloxycarbonylmethyl]-2-bromoethylamine (M. Williams and H. Rapoport, J. Org. Chem. 58, 1151 (1993)) are introduced in 90 ml of acetonitrile and mixed with 70 ml of 2n phosphate buffer solution (pH 8.0). The batch is stirred vigorously at room temperature for 30 hours, and the aqueous phosphate buffer phase is exchanged after 2, 8 and 24 hours for fresh buffer solution. Then, the organic phase is concentrated by evaporation in a vacuum and the residue is chromatographed on silica gel with hexane/ethyl acetate/triethylamine (3:1:0.01). The product-containing fractions are concentrated by evaporation in a vacuum.

Yield: 36.9 g (59% of theory) of colorless solid.

Analysis (taking into consideration the solvent content): Cld: C 60.75, H 9.39, N 6.75; Fnd: C 60.53, H 9.55, N 6.49.

b) 3,6,11,14-Tetraaza-3,14-bis-(carboxymethyl)-6,11-bis-[2-((N,N-bis-carboxymethyl)-amino)-ethyl]-8,9-dihydroxy-hexadecane-1,16-dioic acid 12.8 g (10.3 mmol) of the octaester of Example 10a) is dissolved in 80 ml of methanol and mixed at room temperature with 5.27 g (132 mmol) of sodium hydroxide in 8 ml of water. Then, the reaction mixture is heated to 60° C. and stirred for 5 days. After complete saponification, the solvent is distilled off and the residue is taken up in 150 ml of water. The pH is adjusted to 1 with acid ion exchanger and the batch is stirred for 2 hours at 50° C. until the reaction is completed. After the filtration, the clear aqueous solution is concentrated by evaporation, and the product obtained is absorptively precipitated with isopropanol. After filtration and concentration by evaporation of the filtrate in a vacuum, a colorless oil is obtained.

Yield: 6.8 g (90% of theory)

Analysis (taking into consideration the solvent content): Cld: C 44.44, H 6.39, N 11.11; Fnd: C 44.21, H 6.50, N 10.98.

c) Digadolinium complex of the disodium salt of 3,6,11,14-tetraaza-3,14-bis-(carboxymethyl)-6,11-bis-[2-(N,N-bis-(carboxymethyl)-amino)-ethyl]-8,9-dihydroxy-hexadecane-1,16-dioic acid 5.9 g (7.8 mmol) of the deca acid of Example 10b) is taken up in 100 ml of water, mixed with 1.41 g (3.9 mmol) of gadolinium oxide and stirred for 5 hours at 55° C. Then, it is adjusted to pH 7.2 with diluted sodium hydroxide solution, filtered, and the filtrate is freeze-dried.

Yield: 8.2 g (94.8% of theory) of colorless lyophilizate.

Analysis (relative to solventless substance): Cld: C 30.32, H 3.64, Gd 28.35, N 7.58, Na 4.15; Fnd: C 30.21, H 3.88, Gd 28.09, N 7.43, Na 4.04.

EXAMPLE 11 a) 1,4-Bis-[1-ethoxycarbonyl-2-(2-phthalimidoethyl)-4-(N-phthaloyl)-amino-2-aza-butyl]-benzene 109.52 g (301.4 mmol) of bis(2-phthalimidoethyl)-amine, produced according to E. V. Gramin, J. Org. Chem. USSR 23 (1987): 330, is heated to 100° C. for 5 hours with 41.0 g (100.5 mmol) of 1,4-phenylenebis-(e-bromoacetic acid ethyl ester), 41.66 g (301.4 mmol) of potassium carbonate and a spatula-tip full of sodium iodide in 600 ml of dimethylformamide.

It is concentrated by evaporation in a vacuum, taken up with 800 ml of water and extracted twice with 500 ml of ethyl acetate. The organic phase is dried on magnesium sulfate and concentrated by evaporation in a vacuum. The residue is chromatographed on silica gel [mobile solvent: hexane/acetone (3:1)].

Yield: 36.17 g (37% of theory relative to the ester).

Analysis: Cld: C 66.66, H 4.97, N 8.64; Fnd: C 66.59, H 5.04, N 8.58.

b) 1,4-Bis-[3-oxo-1-(2-aminoethyl)-piperazin-2-yl]-benzene 36.0 g (37 mmol) of the title compound of Example 11a) is mixed in 350 ml of methanol with 22.2 ml (370 mmol) of 80% hydrazine hydrate solution and refluxed for 8 hours. It is cooled to 0° C. in an ice bath and suctioned off from settled precipitate. The filtrate is evaporated Go dryness and the residue is chromatographed on silica gel [mobile solvent: methylene chloride/methanol/33% ammonia solution aq. (4:2:1)].

Yield: 10.94 g (82% of theory) of a light yellow oil.

Analysis: Cld: C 59.98, H 7.83, N 23.31; Fnd: C 59.93, H 7.75, N 23.25.

c) 1,4-Bis-[3-oxo-4-tert-butoxycarbonylmethyl-1-(2-N,N-bis(tert-butoxy-carbonylmethyl)-aminoethyl)-piperazin-2-yl]-benzene 10.5 g (29.13 mmol) of the title compound of Example 11b) is dissolved in 400 ml of tetrahydrofuran under an argon atmosphere. 21.84 g (728.2 mmol) of 80% sodium hydride and 142.1 g (728.2 mmol) of bromoacetic acid-tert-butyl ester are added and heated for 2 days at 60° C. It is cooled in an ice bath and water is carefully added. Then, it is evaporated to dryness in a vacuum and the residue is taken up in 400 ml of water. It is extracted three times with 150 ml of methylene chloride, the organic phase is dried on methylene chloride and concentrated by evaporation in a vacuum. The residue is chromatographed on silica gel [mobile solvent: methylene chloride/methanol (20:1)].

Yield: 19.49 g (64% of theory) of a colorless oil.

Analysis: Cld: C 62.05, H 8.48, N 8.04; Fnd: C 61.97, H 8.53, N 8.00.

d) 1,4-Bis-[3-oxo-4-carboxymethyl-1-(2-N,N-bis(carboxymethyl)-aminoethyl)-piperazin-2-yl]-benzene 19.5 g (18.65 mmol) of the title compound of Example 11c) is dissolved in 150 ml of trifluoroacetic acid and stirred for 1 hour at room temperature. It is evaporated to dryness in a vacuum and the residue from methanol/acetone is recrystallized.

Yield: 11.77 g (89% of theory) of a cream-colored powder.

Analysis: Cld: C 50.84, H 5.69, N 11.86; Fnd: C 50.78, H 5.73, N 11.81.

e) 1,4-Bis-[1-carboxy-2-(2-N,N-bis(carboxymethyl)aminoethyl)-5,5-bis(carboxymethyl)-2,5-diazapentyl]-benzene 11.5 g (16.23 mmol) of the title compound of Example 11d) is dissolved in 300 ml of 5N sodium hydroxide solution and refluxed for 12 hours. It is allowed to cool off to 50° C. and mixed with 244 ml of 1N bromoacetic acid in tetrahydrofuran. Then, it is stirred for 24 hours at 50° C. The solution is evaporated to dryness and then chromatographed on silica gel [mobile solvent: ethanol/conc. aq. ammonia/ water (4:1:1)]. After concentration by evaporation of the main fractions, the ammonium salt is provided by a column with acid ion exchanger and the eluate is freeze-dried.

Yield: 8.66 g (62% of theory) of a colorless amorphous powder.

Analysis (corrected for water): Cld: C 47.44, H 5.62, N 9.76; Fnd: C 47.40, H 5.69, N 9.71.

f) Digadolinium complex of 1,4-bis-[1-carboxy-2-(2-N,N-bis-(carboxymethyl)-aminoethyl)-5,5-bis(carboxymethyl)-2,5-diazapentyl]-benzene [as tetrasodium salt]

8.5 g (9.87 mmol) of the title compound of Example 11e) and 3.58 g (9.87 mmol) of gadolinium oxide are stirred in 80 ml of water for 30 minutes at 80° C. It is cooled off to room temperature and adjusted to pH 7.2 by the addition of 2N sodium hydroxide solution. It is stirred for 30 minutes with some activated carbon at room temperature and then filtered. The filtrate is freeze-dried.

Yield: 12.41 g (100% of theory) of a colorless amorphous powder.

Analysis (corrected for water): Cld: C 32.48, H 3.05, N 6.68, Gd 25.02, Na 7.31; Fnd: C 32.43, H 3.11, N 6.63, Gd 24.96, Na 7.36.

g) Diytterbium complex of 1,4-bis-[1-carboxy-2-(2-N,N-bis-(carboxymethyl)-aminoethyl)-5,5-bis(carboxymethyl)-2,5-diazapentyl]-benzene [as tetrasodium salt]

8.5 g (9.87 mmol) of the title compound of Example 11e) and 3.89 g (9.87 mmol) of ytterbium oxide are stirred in 80 ml of water for 4 days at 80° C. It is cooled off to room temperature and adjusted to pH 7.2 by the addition of 2N sodium hydroxide solution. It is stirred for 30 minutes with some activated carbon at room temperature and then filtered. The filtrate is freeze-dried.

Yield: 12.72 g (100% of theory) of a colorless amorphous powder.

Analysis (corrected for water): Cld: C 31.69, H 2.97, N 6.52, Yb 26.85, Na 7.14; Fnd: C 31.43, H 3.10, N 6.48, Yb 26.71, Na 6.98.

h) Dimanganese(II) complex of 1,4-bis-[1-carboxy-2-(2-N,N-bis-(carboxymethyl)-aminoethyl)-5,5-bis (carboxymethyl)-2,5-diazapentyl]-benzene [as hexasodium salt]

8.5 g (9.87 mmol) of the title compound of Example 11e) and 1.13 g (9.87 mmol) of manganese(II)carbonate are stirred in 80 ml of water for 2 hours at 80° C. It is cooled off to room temperature and adjusted to pH 7.2 by the addition of 2N sodium hydroxide solution. It is stirred for 30 minutes with some activated carbon at room temperature and then filtered. The filtrate is freeze-dried.

Yield: 10.84 g (100% of theory) of a colorless amorphous powder.

Analysis (corrected for water): Cld: C 37.18, H 3.49, N 7.65, Mn 10.00, Na 12.56; Fnd: C 37.03, H 3.58, N 7.55, Mn 9.89, Na 12.40.

EXAMPLE 12

Production of a contrast medium for the nuclear medicine use: Indium(III) complex of N,N'-bis-{2-[N",N"-bis-(carboxymethyl)-amino]-3-[(4-methoxy)-phenyl]-propyl}-N,N'-bis-{2-[N"',N"'-bis-(carboxymethyl)-amino]-ethyl}-meso-2,3-diaminosuccinic acid 1.0 ml of a hydrochloric acid solution of 1.0 mCi indium (III) chloride is adjusted to pH 7.5 with saturated aqueous sodium bicarbonate solution. 2.0 mg (2.0 μmol) of the deca acid produced according to Example 6g) is added, the sample is filtered with a membrane filter and the filtrate is autoclaved in a sealed glass ampoule. The solution is ready for use.

Analysis:

By HPLC of the finished sample on silica gel RP-18 with phosphate buffer solution, it can be shown with the aid of a gamma ray detector that practically 100% of the activity used is contained in the complex.

EXAMPLE 13

Dihafnium complex of N,N,N',N'-tetrakis-{2-[N",N"-bis-(carboxymethyl)-amino]-ethyl}-2,7-diaminooctanedioic acid-N"',N""-bis-(2-methoxyethyl)-diamide a) 2,7-Di(benzyloxycarbonylamino)-octanedioic acid dimethyl ester 9.45 g (20 mmol) Of 2,7-di(benzyloxycarbonylamino)-octanedioic acid (P. M. Fischer et al., TH 50,2277 (1994)) is dissolved in 100 ml of methanol and mixed with 14.6 ml (200 mmol) of thionyl chloride at 0° C. and then stirred overnight at room temperature. It is evaporated to dryness and the residue is taken up in ethyl acetate. At 0° C., it is mixed with saturated sodium bicarbonate solution and the organic phase is separated. The aqueous phase is extracted three times with 50 ml of ethyl acetate each, the combined organic phases are dried on potassium carbonate, filtered and concentrated by evaporation.

Yield: 9.2 g (91.9% of theory)

Analysis (relative to solventless substance): Cld: C 62.39, H 6.44, N 5.60, O 25.57; Fnd: C 62.21, H 6.60, N 5.73.

b) 2,7-Di(benzyloxycarbonylamino)octanedioic acid-bis-(2-methoxyethyl)-diamide

A solution of 9.05 g (18.1 mmol) of 2,7-di (benzyloxycarbonylamino)octanedioic acid dimethyl ester in 30 ml of ethanol is mixed with 6.79 g (90.4 mmol) of 2-methoxyethylamine and refluxed for 14 hours. Then, it is completely concentrated by evaporation and the residue is chromatographed on silica gel with dichloromethane/methanol. After the concentration by evaporation of the product-containing fractions, a slightly yellowish oil is obtained.

Yield: 9.1 g (86.7% of theory)

Analysis (relative to solventless substance): Cld: C 61.42, H 7.22, N 9.55, O 21.82; Fnd: C 61.28, H 7.42, N 9.62.

c) 2,7-Diaminooctanedioic acid-bis-(2-methoxyethyl)-diamide 8.9 g (15 mmol) of the diamide of Example 13b) is dissolved in 30 ml of methanol and hydrogenated for 2 hours at normal pressure with 0.9 g of Pd/C (10%) at room temperature. After the reaction is completed, the catalyst is filtered off and the residue is evaporated to dryness in a vacuum.

Yield: 4.3 g (90% of theory) of yellowish oil.

Analysis (relative to solventless substance): Cld: C 52.81, H 9.50, N 17.59, O 20.10; Fnd: C 52.68, H 9.63, N 17.33.

d) N,N,N',N'-Tetrakis-{2-[N",N"-bis-(benzyloxycarbonylmethyl)-amino]-ethyl}-2,7-diaminooctanedioic acid-N"',N""-bis-(2-methoxyethyl)-diamide 4.2 g (13.2 mmol) of the compound produced according to Example 13c) and 24.9 g (59.4 mmol) of N,N-bis-[(benzyloxycarbonyl)-methyl]-2-bromoethylamine (M. Williams and H. Rapoport, J. Org. Chem. 58, 1151 (1993)) are introduced in 30 ml of acetonitrile and mixed with 22 ml of 2n phosphate buffer solution (pH 8.0). The batch is stirred vigorously at room temperature for 20 hours, and the aqueous phosphate buffer phase is exchanged for fresh buffer solution after 2 and 8 hours. Then, the organic phase is concentrated by evaporation in a vacuum and the residue is chromatographed on silica gel with hexane/ethyl acetate/triethylamine (3:1:0.01). The product-containing fractions are concentrated by evaporation in a vacuum.

Yield: 17.6 g (79.5% of theory) of colorless oil.

Analysis (relative to solventless substance): Cld: C 67.37, H 6.86, N 6.69, O 19.09; Fnd: C 67.19, H 6.92, N 6.74.

e) Dihafnium complex of the N,N,N',N'-tetrakis-{2-[N",N"-bis-(carboxymethyl)-amino]-ethyl}-2,7-diaminooctanedioic acid-N"',N""-bis-(2-methoxyethyl)-diamide 17.4 g (10.4 mmol) of the octaester described in Example 13d) is dissolved in 80 ml of methanol and mixed with 62 ml of 2n sodium hydroxide solution. It is refluxed for 1.5 hours, the methanol is drawn off in a vacuum and stirred for another 3 hours at 60° C. Then, it is adjusted to pH 1 with concentrated hydrochloric acid, evaporated to dryness in a vacuum, and the residue is absorptively precipitated with isopropanol. After filtration and concentration by evaporation of the filtrate in a vacuum, a colorless oil is obtained, which is taken up in 80 ml of water and mixed with 5.1 g (20.8 mmol) of hafnium hydroxide (produced from hafnium oxychloride octahydrate according to the instructions of D. J. Williams et al., J. Chem. Soc. Dalton Trans. 2475, 1992). It is refluxed for 72 hours, then the aqueous solution is stirred with 3.5 g of activated carbon and filtered. The filtrate is somewhat concentrated by evaporation and freeze-dried.

Yield: 12.3 g (90.7% of theory) of colorless lyophilizate.

Analysis (relative to solventless substance); Cld: C 35.00, H 4.48, N 8.59, O 24.54, Hf 27.38; Fnd: C 34.86, H 4.69, N 8.37, Hf 27.11.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. Compounds of general formula I, consisting of increments (A) and (B):

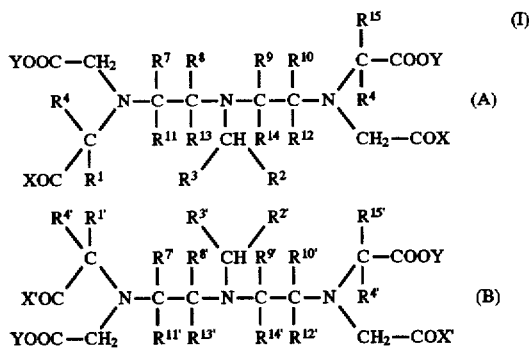

in which increments A and B are linked together by a substituent pair selected from the group consisting of $R^1$ and $R^{1'}$, $R^2$ and $R^{2'}$, $R^{15}$ and $R^{15'}$, $R^1$ and $R^{2'}$, $R^{1'}$ and $R^2$, $R^{1'}$ and $R^{15}$, $R^1$ and $R^{15'}$, $R^2$ and $R^{15'}$ and $R^{2'}$ and $R^{15}$, in which the substituent pair linked is selected from the group consisting of a heterocycle, a phenylene radical, a $C_0-C_{30}$ alkylene chain, and a $C_7-C_{30}$ aralkylene chain, which optionally is substituted by 1-4 hydroxy, $C_1-C_6$ alkoxy, carboxy or mercapto groups and/or is interrupted by 1 to 6 components selected from the group consisting of oxygen, nitrogen, sulfur atoms, sulfinyl and sulfonyl groups, wherein the substituents $R^1$, $R^{1'}$, $R^{15}$, $R^{15'}$ not required for linkage, independently of one another, are selected from the group consisting of a hydrogen atom and $C_1-C_6$ alkyl groups optionally substituted by 1-4 hydroxy or mercapto groups, wherein the substituents $R^2$ and $R^{2'}$ not required for linkage, independently of one another, are selected from the group consisting of a hydrogen atom, $C_1-C_6$ alkyl groups, —$(CH_2)_n$OH and —$(CH_2)_n$SH where n=1 or 2, where the substituents $R^3$ and $R^{3'}$, independently of one another, are selected from the group consisting of a COOY group and a $CONR^5R^6$ group, in which $R^5$ and $R^6$, independently of one another, mean a $C_1-C_6$ alkoxy group which optionally is substituted by 1-4 hydroxy or $C_{1-6}$ alkoxy groups and/or is interrupted by 1-6 components selected from the group consisting of oxygen, nitrogen and sulfur atoms, or $NR^5R^6$ is a 5- or 6-membered ring which contains nitrogen, which optionally contains an oxygen atom, another acylated nitrogen atom or a sulfonyl group and/or is substituted with 1-3 hydroxy groups, where the substituents $R^4$ and $R^{4'}$ are selected from the group consisting of a hydrogen atom and $C_1-C_6$ alkyl groups, and the substituents, $R^7$, $R^8$, $R^9$, $R^{10}$, $R^{11}$, $R^{12}$, $R^{13}$ and $R^{14}$ and $R^{7'}$, $R^{8'}$, $R^{9'}$, $R^{10'}$, $R^{11'}$, $R^{12'}$, $R^{13'}$ and $R^{14'}$ are selected from the group consisting of a hydrogen atom, a phenyl group, $C_1-C_{30}$ alkyl chains and $C_7-C_{30}$ aralkyl chains, which optionally is substituted by 1-4 hydroxy, $C_1-C_6$ alkoxy or mercapto groups and/or is interrupted by 1-6 components selected from the group consisting of oxygen, nitrogen and sulfur atoms, or the following substituent pairs combine together to form a trimethylene or tetramethylene group: $R^7$ combined with $R^8$, $R^{7'}$ combined with $R^{8'}$, $R^9$ combined with $R^{10}$ and $R^{9'}$ combined with $R^{10'}$, Y is selected from the group consisting of a hydrogen atom and metal ion equivalents of an element of atomic numbers 21–32, 37–39, 42–51 and 57–83, wherein at least two of substituents Y are metal ion equivalents of at least one element of atomic numbers 21–32, 37–39, 42–51 and 57–83, and X and X' are selected from the group consisting of —OY, and —$CONR^5R^6$, with Y, $R^5$ and $R^6$ as defined above, as well as their salts with inorganic bases, organic bases or amino acids.

2. Compounds according to claim 1, wherein the linkage of increments (A) and (B) takes place with substituent pairs $R^1$, $R^{1'}$; $R^2$, $R^{2'}$; $R^{15}$, $R^{15'}$; $R^1$, $R^{2'}$ or $R^{1'}$, $R^2$.

3. Compounds according to claim 1, wherein substituent pair $R^2$, $R^{2'}$ represents a direct bond, a $C_1-C_{30}$ alkylene chain, a $C_7-C_{30}$ aralkylene chain which is interrupted by two oxygen atoms, or a phenylene radical.

4. Compounds according to claim 1, wherein substituent pair $R^1$, $R^{1'}$ represents a $C_2-C_{30}$ alkylene chain interrupted by an oxygen atom.

5. Compounds according to claim 1, wherein the substituent pair $R^1$, $R^{2'}$ represents a $C_7-C_{30}$ alkylene chain interrupted by an oxygen atom.

6. A diagnostic agent, containing at least one compound according to claim 1.

7. Process for the production of compounds of formula I according to claim 1, in which Y is a metal ion equivalent of an element of atomic numbers 21–32, 37–39, 42–51 and 57–83, said process comprising reacting compounds of formula I according to claim 1, in which Y is a hydrogen atom, with a metal salt or metal oxide of an element of the atomic numbers 21–37, 37–39, 42–51 and 57–83.

8. A method of diagnosis which comprises administering to a patient a metal complex according to claim 1 and performing NMR diagnosis or diagnostic radiology on said patient.

9. A method of using at least one metal complex according to claim 1 for radiodiagnosis or radiotherapy of a patient which comprises administering a metal complex according to claim 1 to a patient.

10. A metal complex according to claim 1, which is the digadolinium complex of the tetrasodium salt of N,N,N',N'-tetrakis-{2-[N'',N''-bis-(carboxymethyl)-amino]-ethyl}-meso-2,3-diaminosuccinic acid.

11. A metal complex according to claim 1, which is the digadolinium complex of the tetrasodium salt of N,N,N',N'-tetrakis-{2-[N'',N''-bis-(carboxymethyl)-amino]-ethyl}-meso-2,6-diaminopimelic acid.

12. A metal complex according to claim 1, which is the diytterbium complex of the tetrasodium salt of 3-{4-{2-N, N-bis-{2-{N',N'-bis-(carboxymethyl)-amino]-ethyl]}-amino-2-carboxyethyl]-phenoxy}-2-{N-{2-[N'-[2-[N'',N''-bis-(carboxymethyl)-amino]-ethyl]-N'-(carboxymethyl)-amino]-ethyl}-N-(carboxymethyl)-amino}-propionic acid.

13. A metal complex according to claim 1, which is the digadolinium complex of the disodium salt of N,N,N',N'-tetrakis-{2-[N",N"-bis-(carboxymethyl)-amino]-ethyl}-meso-2,3-diaminosuccinic acid-N"',N""-bis-(2-methoxyethyl)-diamide.

14. A metal complex according to claim 1, which is the digadolinium complex of the tetrasodium sodium salt of 1,8-bis-{4-[2-(N,N-bis-(2-(N',N'-bis-(carboxymethyl)-amino)-ethyl)-amino)-2-carboxyethyl]-phenoxy}-octane.

15. A metal complex according to claim 1, which is the didysprosium complex of the tetrasodium salt of N,N'-bis-{2-[N",N"-bis-(carboxymethyl)-amino]-3-[(4-methoxy)-phenyl]-propyl}-N,N'-bis-{2-[N"',N"'-bis-(carboxymethyl)-amino]-ethyl}-meso-2,3-diaminosuccinic acid.

16. A metal complex according to claim 1, which is the digadolinium complex of the tetrasodium salt of 3,6,9,15,18,21-hexaaza-10,14-bis-carboxy-3,6,9,15,18,21-hexakis-(carboxymethyl)-12-oxa-tricoxane-1,23-dioic acid.

17. A metal complex according to claim 1, which is the didysprosium complex of N,N,N',N'-tetrakis-{2-[[N"-(carboxymethyl)]-N"-((N"'-methyl)-carbamoylmethyl)-amino]-ethyl}-meso-2,6-diaminopimelic acid.

18. A metal complex according to claim 1, which is the digadolinium complex of the tetrasodium salt of the N,N,N',N'-tetrakis-{2-[N",N"-bis-(carboxymethyl)-amino]-2-(hydroxymethyl)-propyl}-meso-2,3-diaminosuccinic acid.

19. A metal complex according to claim 1, which is the digadolinium complex of the tetrasodium salt of 1,4-bis-{1-carboxy-2-[2-N,N-bis(carboxymethyl)aminoethyl]-5,5-bis(carboxymethyl)-2,5-diazapentyl}-benzene.

20. A metal complex according to claim 1, which is the diytterbium complex of the tetrasodium salt of 1,4-bis-{1-carboxy-2-[2-N,N-bis(carboxymethyl)aminoethyl]-5,5-bis(carboxymethyl)-2,5-diazapentyl}-benzene.

21. A metal complex according to claim 1, which is the dimanganese complex of the hexasodium salt of 1,4-bis-{1-carboxy-2-[2-N,N-bis(carboxymethyl)aminoethyl]-5,5-bis(carboxymethyl)-2,5-diazapentyl}-benzene.

22. A metal complex according to claim 1, which is the indium(III) complex of N,N'-bis-{2-[N",N"-bis-(carboxymethyl)-amino]-3-[(4-methoxy)-phenyl]-propyl}-N,N'-bis-{2-[N"',N"'-bis-(carboxymethyl)-amino]-ethyl}-meso-2,3-diaminosuccinic acid.

23. A metal complex according to claim 1 which is the dihafnium complex of N,N,N',N'-tetrakis-[2-[N",N"-bis-(carboxymethyl)-amino]ethyl]-2,7-diaminooctanedioic acid-N"',N""-bis(2-methoxyethyl)-diamide.

* * * * *